(12) United States Patent
Trafalis

(10) Patent No.: US 10,208,083 B2
(45) Date of Patent: Feb. 19, 2019

(54) ESTERS OF STEROIDAL LACTAM AND BIS(2-CHLOROETHYL) AMINOPHENOXY PROPANOIC ACID DERIVATIVES

(71) Applicants: GALENICA S.A., Kifissia (GR); ENERGONBIO TECHNOLOGIES S.A., Nikaia (GR)

(72) Inventor: Dimitrios Trafalis, Nikaia (GR)

(73) Assignees: Galenica S.A., Kifissia (GR); Energonbio Technologies S.A., Nikaia (GR)

( * ) Notice: Subject to any disclaimer, the term of this patent is extended or adjusted under 35 U.S.C. 154(b) by 0 days.

(21) Appl. No.: 15/738,328

(22) PCT Filed: Jun. 28, 2016

(86) PCT No.: PCT/EP2016/065071
§ 371 (c)(1),
(2) Date: Dec. 20, 2017

(87) PCT Pub. No.: WO2017/001439
PCT Pub. Date: Jan. 5, 2017

(65) Prior Publication Data
US 2018/0194800 A1    Jul. 12, 2018

(30) Foreign Application Priority Data
Jun. 29, 2015    (EP) .................................... 15386022

(51) Int. Cl.
*A61P 35/02*    (2006.01)
*C07J 73/00*    (2006.01)

(52) U.S. Cl.
CPC ............. *C07J 73/005* (2013.01); *A61P 35/02* (2018.01)

(58) Field of Classification Search
CPC ........ C07J 73/005; A61P 35/00; A61P 35/002
See application file for complete search history.

(56) References Cited

PUBLICATIONS

I. Kline et al., "Experimental Evaluation of Antitumor Drugs in the USA and USSR and Clinical Correlations", National Cancer Institute Monograph, 1980; (55), pp. 1-179.
A. Papageorgiou et al., "Structure—anti-leukemic activity relationship study of B- and D-ring modified and non-modified steroidal esters of chlorambucil's active metabolite", Anti-Cancer Drugs, 2005, vol. 16 No. 10, pp. 1075-1082.
I. Papaconstantinou, "Steroidal esters of the aromatic nitrogen mustard 2-[4-N,N-bis(2-chloroethyl)amino-phenyl]butanoic acid (2-PHE-BU): synthesis and in-vivo biological evaluation", Anti-Cancer Drugs, 2013, vol. 24 No. 1, pp. 52-65.
P. Catsoulacos et al., "On the Formation of Estrone Lactam Esters of N,N-Bis(2-chloroethyl)aminocinnamic Acid Isomers, p-N,N-Bis(2-chloroethyl)aminophenylbutyric Acid and Their Antitumor Activity", J. Heterocyclic, 32, 1995, pp. 1063-1065.
M. Efthimiou et al., "Comparative study of genetic activity of chlorambucil's active metabolite steroidal esters: The role of steroidal skeleton on aneugenic potential", Mutation Research 689, 2010, pp. 1-11.
A. Kapou et al., "3D QSAR/CoMFA and CoMSIA Studies on Antileukemic Steroidal Esters Coupled with Conformationally Flexible Nitrogen Mustards", J. Chem. Inf. Model., 2008, 48, pp. 2254-2264.
Laurence H. Hurley, www.nature.com/reviews/cancer, "DNA and its associated processes as targets for cancer therapy", Mar. 2002, vol. 2, pp. 188-200.
M. Brendel et al., "Relationships between functionality and genetic toxicology of selected DNA-damaging agents", Mutation Research, 133, 1984, Elsevier, p. 51-85.
M. Wall et al., "The Effects of Some Steroidal Alkylating Agents on Experimental Animal Mammary Tumor and Leukemia Systems", vol. 12, Sep. 1969, pp. 810-818.
K. Matsumoto et al., "Efficacy of estramustine phosphate sodium hydrate (EMP) monotherapy in castration-resistant prostate cancer patients: report of 102 cases and review of literature", Med Oncol (2013) 30:717, pp. 1-7.
"Prednimustine", IARC Monographs vol. 50, pp. 115-122.
W. Hiddemann, "Non-Hodgkin's Lymphomas—Current Status of Therapy and Future Perspectives", European Journal of Cancer, vol. 31A, Nos. 13/14, pp. 2141-2145, Jun. 1995.
Dr. P. Catsoulacos, "Comparison of Current Alklating Agents with a Homo-aza-Steroidal Ester for Antineoplastic Activity", Oncology, 1994; 51, pp. 74-78.
C. Camoutsis et al., "An overview on the antileukemic potential of D-homo-aza- and respective 17 β-acetamido-steroidal alkylating esters", Investigational New Drugs, 21, pp. 47-54, 2003.
A. Koutsourea et al., "Rational design, synthesis, and in vivo evaluation of the antileukemic activity of six new alkylating steroidal esters", Bioorganic & Medicinal Chemistry, 16, 2008, pp. 5207-5215.
R. Mazur, "Azasteroids. III. 3-Aza-A-homo Androgens", Notes, vol. 28, Aug. 1962, pp. 248-250.
J. Morzycki et al., "Synthesis of 4,17-Diazasteroid Inhibitors of Human 5α-Reductase", Bioorganic & Medicinal Chemistry, vol. 4, No. 8, pp. 1209-1215, 1996.
C. Camoutsis et al., "Beckmann Rearrangement of 3-Aza-A-homo-4α-androsten-4,17-dione Oxime and 3-Oxo-13α-amino-13,17-sero-4-androsten-17-oic 13,17-Lactam Oxime", J. Heterocyclic Chem., vol. 20, Jul.-Aug. 1983, pp. 1093-1094.
Y. Huang et al., www.mdpi.com/journal/molecules, "Synthesis and Evaluation of Some 17-Acetamidoandrostane and N,N-Dimethyl-7deoxycholic Amide Derivatives as Cytotoxic Agents: Structure/Activity Studies", Molecules 2013, 18, pp. 7436-7447.
K. Valu et al., "DNA-Directed Alkylating Agents. 3. Structure-Activity Relationships for Acridine-Linked Aniline Mustards: Consequences of Varying the Length of the Linker Chain", Journal of Medicinal Chemistry, 1990, vol. 33, No. 11, pp. 3014-3019.

(Continued)

*Primary Examiner* — Barbara P Badio
(74) *Attorney, Agent, or Firm* — Davis & Bujold PLLC; Michael J. Bujold

(57) ABSTRACT

Novel homo-aza-steroidal esters with alkylating bis(2-chloroethyl)aminophenoxy propanoic acid and substituted derivatives, processes for their preparation, pharmaceutical compositions containing them and use thereof in the treatment of cancer.

10 Claims, No Drawings

(56) References Cited

PUBLICATIONS

T. Ivanenko et al., "Synthesis and Properties of 17-N-Substituted Derivatives of 1,3,5(10)-Estratrienes", Institute of Experimental Endocrinology and Hormone Chemistry, Academy of Medical Sciences of the USSR, Moscow, vol. 16, No. 10, Oct. 1982, pp. 751-756.

B. Regan et al., "17- and 17a-Aza-D-homosteroids", Contribution from the Department of Chemistry of Illinois Institute of Technology, vol. 78, Feb. 5, 1956, pp. 639-643.

A. Koutsourea et al., www.sciencedirect.com, "Synthetic approaches for the synthesis of a cytostatic steroidal B-D bilactam", Steroids, 68, 2003, pp. 659-666.

D.T.P. Trafalis et al., "Preclinical evaluation of the homo-aza-steroid ester 13β-hydroxy-13α-amino-13,17-seco-5α-androstan-17-oic-13,17-lactam-p-bis(2-chloroethyl)aminophenoxy acetate for the treatment of malignant melanoma", Journal of BUON, 8, pp. 333-339, 2003.

D.T. Trafalis et al., "Antitumour effect of a- and d-lactam androgen nitrogen mustards on non-small cell lung caranoma", Journal of BUON, 9, pp. 275-282, 2004.

D.T.P. Trafalis et al., "A preclinical survey on the efficacy of lactandrate in the treatment of colon carcinoma", Journal of BUON, 10, pp. 227-234, 2005.

D.T.P. Trafalis et al., "Lactandrate: a D-homo-aza-androsterone alkylator in the treatment of breast cancer", Breast Cancer Research and Treatment, 2006, 97, pp. 17-31.

P. Catsoulacos et al., "A New Steroidal Alkylating Agent with Improved Activity in Advanced Murine Leukemias", Cancer Chemotherapy and Pharmacology, 3, pp. 67-70, 1979.

P. Catsoulacos et al., "New Compounds: Antitumor Activity of 3β-Hydroxy-13α-amino-13,17-seco-5α-androstan-17-oic-13,17-lactam 4[p-[Bis(2-chloroethyl)amino]phenyl]butyrate", Journal of Pharmaceutical Sciences, vol. 67, No. 9, Sep. 1978, pp. 1342-1343.

G. Wampler et al., "Antileukemic Effect of Homo-aza-steroidal Ester of [p-[Bis(2-chloroethyl)amino]phenyl]Acetic Acid", Cancer Treatment Reports, vo. 61, No. 1, Jan./Feb. 1977, pp. 37-41.

P. Catsoulacos et al., "Potential Antitumor Agent: Steroidal Bilactam Ester of p-N, N-Bis (2-chloroethyl) aminophenylacetic Acid", Anticancer Research, 15, pp. 827-830, 1995.

P. Catsoulacos et al., "Hybrid Anticancer Compounds. Steroidal Lactam Esters of Cardoxylic Derivatives of N,N-Bis (2-chloroethyl) aniline (Review)", Anticancer Research, 11, pp. 1773-1778, 1991.

P. Catsoulacos et al., "Antitumor Activity of Homo-aza-steroidal Esters of p-N, N-Bis(2-chloroethyl) aminophenoxyacetic Acid", Anticancer Research, 13, pp. 1203-1208, 1993.

P. Catsoulacos et al., "Conjugated System of Homo-aza-steroidal Esters in Cancer Chemotherapy", Anticancer Research, 14, pp. 2525-2528, 1994.

R. Catane, "Clinical Experience With Estramustine, Phosphate and Prednimustine, Two Steroidal Alkylating Agent Compounds", National Cancer Institute, Cancer Treatment Reports, vol. 62, No. 8, Aug. 1978, pp. 1264-1265.

Kline and Platonova, "Experimental Evaluation of Antitumor Drugs in the USA and USSR and clinical correlations", National Cancer Institute (NCI) Monograph, 55, pp. 25-26, 1980.

ESTERS OF STEROIDAL LACTAM AND BIS(2-CHLOROETHYL) AMINOPHENOXY PROPANOIC ACID DERIVATIVES

FIELD OF THE INVENTION

The present invention relates to novel homo-aza-steroidal esters with alkylating mustards, derivatives of aniline, such as bis(2-chloroethyl)aminophenoxy propanoic acid and substituted derivatives.

BACKGROUND OF THE INVENTION

Nowadays, alkylating anticancer agents, as nitrogen mustards, still remain an effective class of antitumor drugs in current clinical practice, whose therapeutic effects derive from their ability to attach alkyl groups to cellular DNA and to produce significant DNA damage (Hurley L H, Nature Rev Cancer, 2002, 2:188-200; Brendel M and Ruhland A, Mutat Res, 1984; 133:51-85).

Steroidal conjugates have been previously used as carriers of cytotoxic alkylating agents because they reduce systemic toxicity and improve efficacy of cancer therapy (Wall M E et al, J Med Chem, 1969, 12:810-8; Catane R, Cancer Treat Rep, 1978; 62:1264-5). Steroidal alkylating agents as Estramustine (ester of estradiol and mechlorethamine) and Prednimustine (ester prednisolone and chlorambucil) are currently applied in cancer therapy on the treatment of prostate cancer and lymphoproliferative malignancies respectively (Catane R, Cancer Treat Rep, 1978, 62:1264-5; Matsumoto K et al, Med Oncol, 2013, 30:717; IARC Monogr Eval Carcinog Risks Hum, 1990, 50:115-22; Hiddemann W, Eur J Cancer, 1995, 31A (13-14):2141-5).

Several homo-aza- or lactam steroidal esters (steroids that contain lactam group —NHC=O— into steroid ring/s conjugated with alkylating agents) have been previously synthesized and tested for toxicity and anticancer activity in preclinical settings, in vitro and in vivo (Wampler G L and Catsoulacos P, Cancer Treat Rep, 1977, 61:37-41; Catsoulacos P and Catsoulacos D, Anticancer Res, 1991, 11:1773-7; Catsoulacos P and Catsoulacos D, Anticancer Res, 1993, 13 (4):1203-8; Catsoulacos P et al, Oncology, 1994, 51:74-8; Catsoulacos P and Catsoulacos D, Anticancer Res, 1994, 14 (6B):2525-8; Camoutsis C and Trafalis D T, Invest New Drugs, 2003, 21:47-54; Koutsourea A I et al, Bioorg Med Chem, 2008, 16:5207-15).

Lactam steroid alkylating esters showed that they generate significantly decreased acute toxicity in vivo, whereas they demonstrated enhanced and very promising antitumor activity in vitro and in vivo, while the respective unmodified (non-lactam) steroidal alkylators produced significantly lower or little anticancer activity against the respective experimental tumor systems. Except of the production of cellular DNA damage, the molecular pharmacological mechanisms that significantly improved anticancer effect of the lactam steroid alkylating esters take action are still uncharted. Moreover, the biological importance of the position that one or more lactam groups are incorporated into the steroidal structure is also unknown. Furthermore, the alkylating agent that conjugated via esteric bond on the lactamic steroid plays significant role and modulates the proportion of

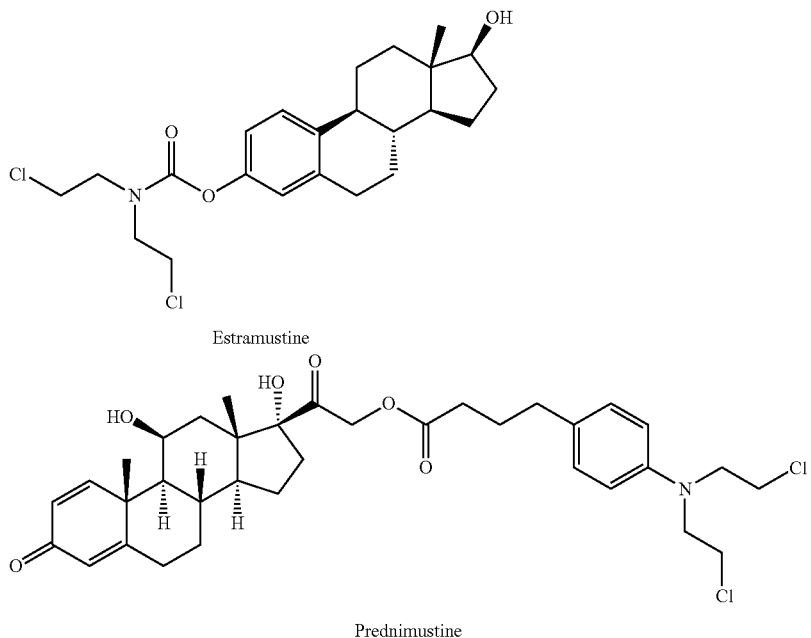

Estramustine

Prednimustine

Whereas these drugs produce diminished acute and systemic toxicity contrary to the much higher toxicity that their alkylating components produced alone, their anticancer activity is not so much improved as well as specificity to targeting cancer cells rather be short despite the initial evaluations. However, even if the main molecular pharmacological mechanisms that estramustine and prednimustine exert anticancer activity are rather different than specific action on the steroid receptors, in general they showed good and improved therapeutic efficacy in clinical practice.

acute toxicity and antitumor activity, and consequently the extent of therapeutic ratio that a lactam steroidal alkylator generates. Up to now, several active lactam steroidal alkylators have been synthesized and tested but those which showed higher antitumor activity were more toxic and those which demonstrated lower toxicity were less active. These observations indicate that there is a clear need to develop and produce novel active lactam steroidal alkylating conjugates that generate optimal the lower toxicity and higher anticancer activity and therefore the optimum therapeutic index.

Previous studies on lactam steroidal alkylating esters of nitrogen mustard derivatives showed that 3beta-hydroxy-13alpha-amino-13,17-seco-5alpha-androstan-17-oic-13,17-lactam-[p-[bis (2-chloroethyl)amino]phenyl]acetate (ASE, NSC-290205) produced very well balanced effects in preclinical testing on acute toxicity in vivo and antitumor activity in vitro and in vivo, holding a significantly high therapeutic index.

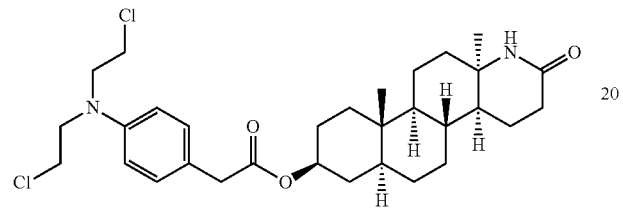

3beta-hydroxy-13alpha-amino-13,17-seco-5alpha-androstan-17-oic-13,17-lactam -[p-[bis (2-chloroethyl)amino]phenyl]acetate (ASE, NSC-290205)

Therefore ASE represented the "golden" standard for developing new molecules of the same class of agents and testing them for therapeutic efficacy in comparison to that of ASE.

SUMMARY OF THE INVENTION

The present invention provides novel esters of steroidal lactams and alkylating agents. More specifically, the compounds of the present invention are esters of steroidal lactams with derivatives of bis(2-chloroethyl)aminophenoxypropanoic acid. These compounds exhibit higher antitumor activity and lower acute toxicity in comparison with lactam steroid alkylating esters of the prior art and are useful as antineoplastic agents and cancer therapeutics.

DETAILED DESCRIPTION OF THE INVENTION

The present invention provides a compound of formula (I) or a pharmaceutically acceptable salt thereof

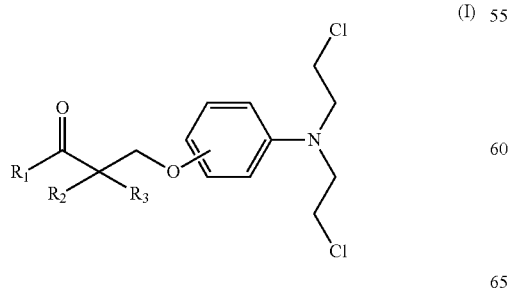

(I)

wherein $R_1$ is selected from the group consisting of

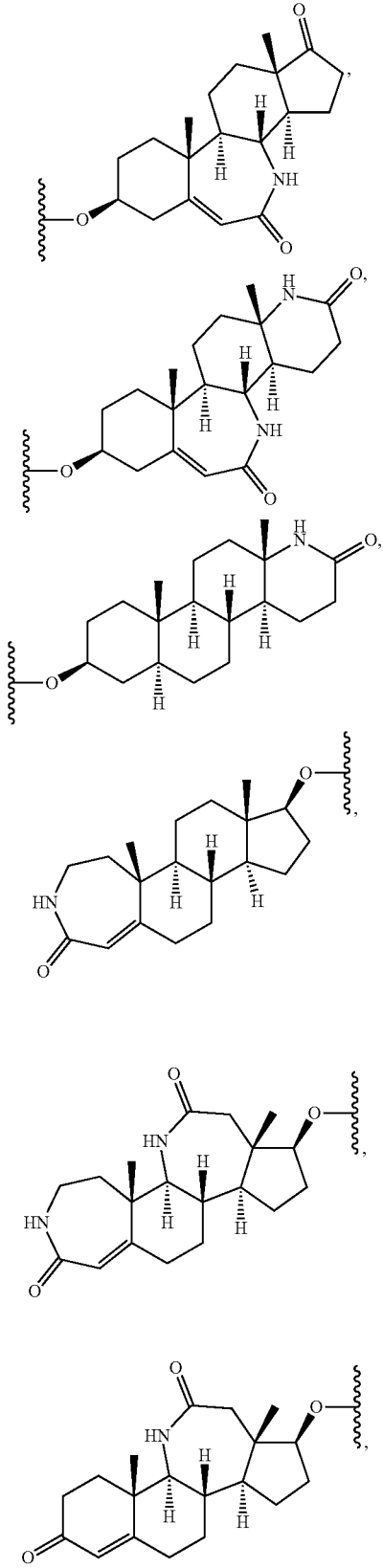

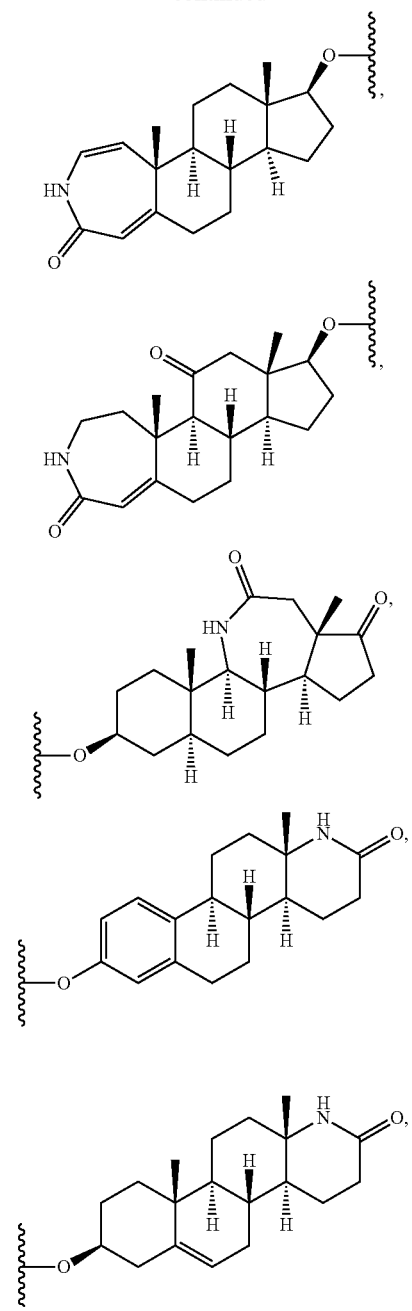
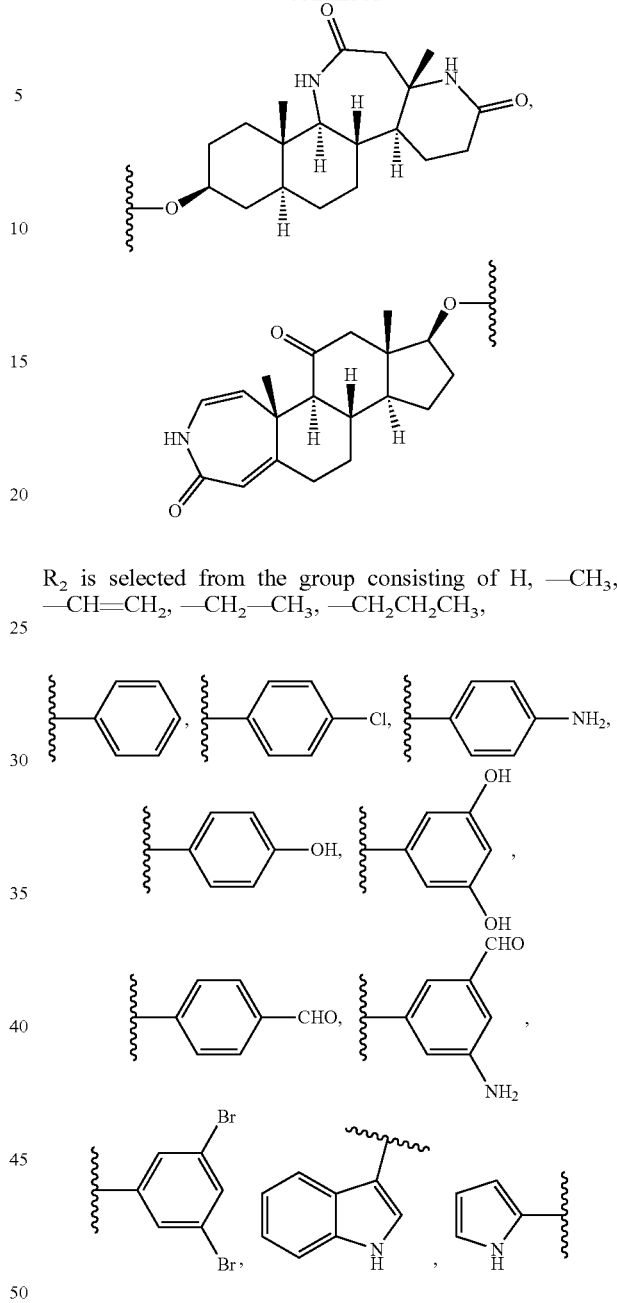
$R_2$ is selected from the group consisting of H, —CH$_3$, —CH=CH$_2$, —CH$_2$—CH$_3$, —CH$_2$CH$_2$CH$_3$,
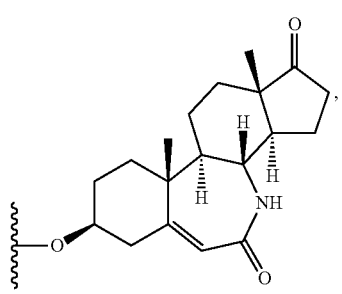
$R_3$ is selected from the group consisting of H, —OH, —NH$_2$.
Preferably, $R_1$ is selected from the group consisting of
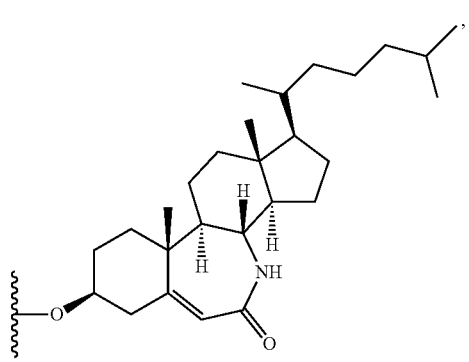

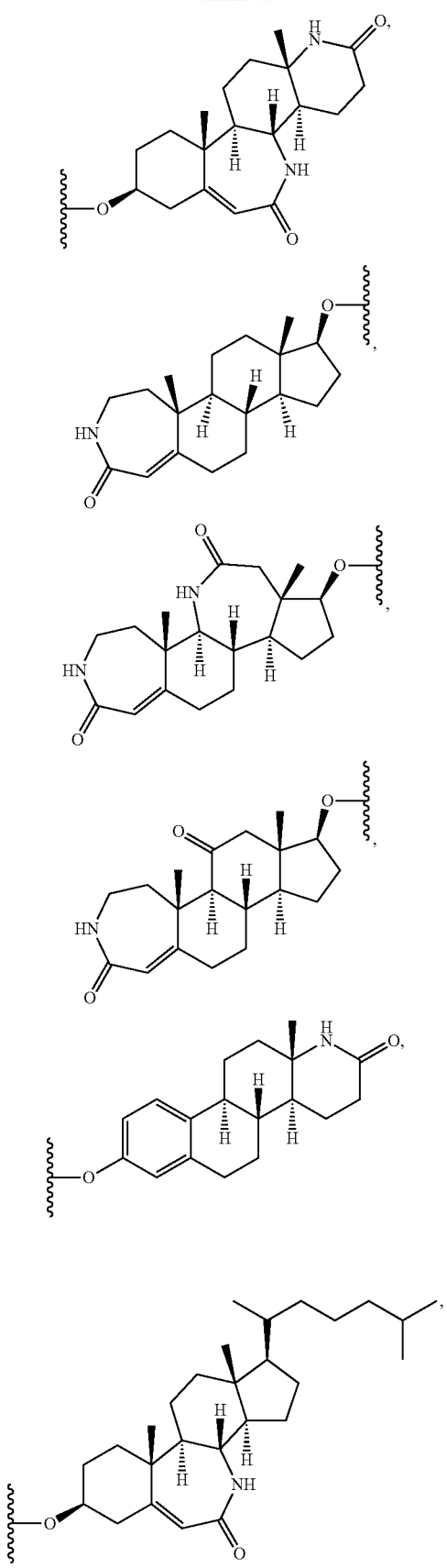
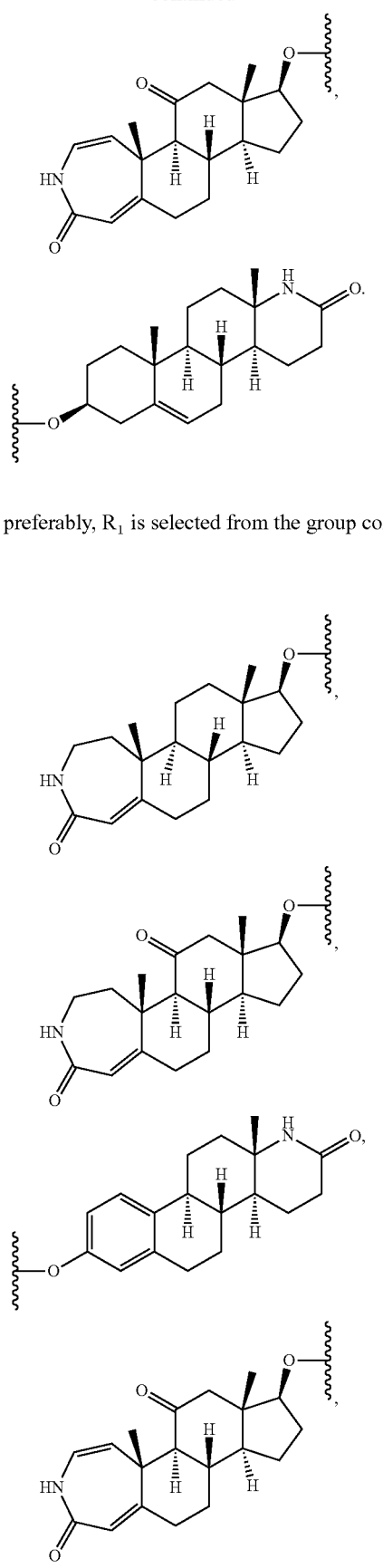
More preferably, $R_1$ is selected from the group consisting of -continued

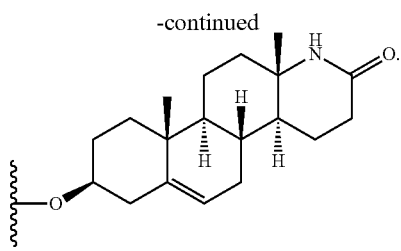

Preferably, $R_2$ is selected from the group consisting of H, —$CH_3$, —CH=$CH_2$, —$CH_2$—$CH_3$, —$CH_2CH_2CH_3$. More preferably, $R_2$ is H.

Preferably, $R_3$ is H or $NH_2$.

The hydroxyl group of the bis(2-chloroethyl)aminophenol moiety of the compounds of formula (I) can be in the ortho-, meta-, or para-position in relation to the amino group of the phenyl ring.

The compounds of formula (I) contain at least one asymmetric center. Where the stereochemistry of an asymmetric center is not specified, the structure is intended to encompass all individual stereoisomers as well as their mixtures.

The compounds of formula (I) contain at least one basic functional group and are capable therefore for forming pharmaceutically acceptable salts by treatment with a suitable acid. Suitable acids include pharmaceutically acceptable inorganic and pharmaceutically acceptable organic acids. Examples of pharmaceutically acceptable salts include hydrochloride, hydrobromide, sulfate, phosphate, nitrate, acetate, propionate, butyrate, maleate, fumarate, tartrate, citrate, lactate, oxalate, succinate, and benzoate.

The compounds of formula (I) or their pharmaceutically acceptable salts can be used for the treatment of a wide range of cancers. Preferably, they are used for the treatment of ovarian, breast, prostate cancer or leukemia.

The compounds of formula (I) or their pharmaceutically acceptable salts exhibit higher antitumor activity and lower acute toxicity in comparison with lactam steroid alkylating esters of the prior art and are useful as antineoplastic agents and cancer therapeutics. The preclinical testing for biological activity disclosed in the examples hereinafter incorporates in comparison and in order to show the superiority of the new alkylating lactam steroidal esters on cancer therapeutic efficacy two positive controls, the alkylating agent (3-(4-(bis(2-chloroethyl) amino)phenoxy)propanoic acid, pBCEAPOPA) alone, and the "golden" standard of the described class of experimental lactam steroidal alkylators, ASE (NSC-290205).

The present invention provides also pharmaceutical compositions comprising a compound of formula (I) or a pharmaceutically acceptable salt thereof. Such a pharmaceutical composition may be formulated for administration by any appropriate route such as oral, nasal, topical or parenteral route. For example, a pharmaceutical composition may be formulated as tablet, capsule, powder, solution, suspension, cream or gel. Such a composition generally contains, in addition to a compound of formula (I) or a pharmaceutically acceptable salt thereof, a pharmaceutically acceptable carrier. Such a carrier comprises excipients well known in the art, such as diluents, binders, fillers, disintegrants, lubricants, solvents, suspending agents, thickening agents, buffers, preservatives. These compositions may be prepared following methods well known in the art.

The present invention provides also processes for the preparation of a compound of formula (I) or a pharmaceutically acceptable salt thereof.

The steroidal lactams (aza-homo steroids) in the compounds of formula (I) carry one or more amide functionalities at the rings of the basic steroidal framework. It is known that such steroidal lactams can be synthesized from a ketosteroid via the corresponding oximes and Beckman rearrangement (Koutsourea A I et al, Steroids, 2003, 68 (7-8):659-66; Mazur R H, J Org Chem, 1963, 28 (1):248-250; Morzycki J W et al, Bioorg Med Chem, 1996, 4 (8): 1209-15; Camoutsis C and Catsoulacos P, J Heterocycl Chem, 1983, 20 (4):1093-4; Huang Y et al, Molecules, 2013, 18 (7):7436-47).

General Procedure for the Beckmann Rearrangement

The oximes (1 mmol) were dissolved in 17.5 mL of dry dioxane. The mixture was cooled to 0° C. and thionyl chloride (1.9 mL) was added dropwise. The mixture was allowed to reach room temperature and stirred for 24 h. The reaction was quenched with $NaHCO_3$ and the mixture was extracted with ethyl acetate (3×20 mL). The organic layers were dried ($Na_2SO_4$) and concentrated under reduced pressure to afford the crude product that was further purified by chromatography on $SiO_2$.

The bis(2-chloroethyl)aminophenoxy propanoic acid derivatives of the compounds of the present invention can be prepared as follows:

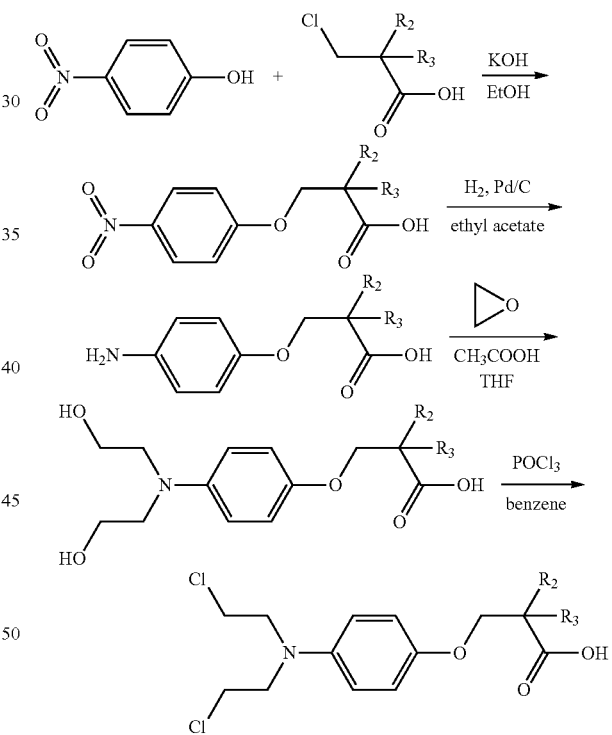

Substituted 3-(4-(bis(2-chloroethyl)amino)phenoxy)propanoic acids were synthesized starting from 4-nitrophenol. Alkylation of 4-nitrophenol with different 3-chloropropanoic acids gave the 3-(4-nitrophenoxy)propanoic acids, which were further reduced to amino derivatives by using $H_2$ and Pd/C as catalyst. Next, the amino group was bis-alkylated with oxirane in $CH_3COOH$, THF following a known procedure (Valu et al, J Med Chem, 1990, 33 (11): 3014-19). Finally, the alcohol groups were transformed to the corresponding chlorides by using $POCl_3$ in benzene and heating, affording the corresponding 3-(4-(bis(2-chloroethyl)amino) phenoxy)propanoic acids. In some cases, when amino or hydroxyl groups are present, extra steps for the protection and the deprotection reactions are necessary. For example when R3 is NH₂ or OH group the Boc or Acetyl protecting groups are used respectively (Valu K K et al, J Med Chem, 1990, 33 (11):3014-9). Following the same process, and starting from 2-nitrophenol or 3-nitrophenol, derivatives of formula (I) in which the hydroxyl group is in ortho- or meta-position in relation to the amino group can be synthesised.

For the production of the steroidal lactam esters with alkylating agents the steroidal lactams containing a OH group react with the DNA alkylating agent. For example a steroidal lactam reacts with the 3-(4-(bis(2-chloroethyl)amino)phenoxy)propanoic acid with DCC, DMAP or with 3-(4-(bis(2-chloroethyl)amino)phenoxy)propanoyl chloride or with a mixed anhydride of 3-(4-(bis(2-chloroethyl)amino)phenoxy)propanoic acid to produce the corresponding esters. Any steroidal mono- or bis-lactam can be derivatized using the present method.

General Procedure A for the Esterification of Steroidal Lactams

Alcohol (1 mmol) was dissolved in 28 mL of dry dichloromethane. Then, acid (2 mmol), DCC (2 mmol) and a catalytic amount of DMAP (3 mol %) were added. After the resulting solution was stirred at room temperature for 24 h the solvent was evaporated and the residue was purified by flash column chromatography on silica gel.

General Procedure B for the Esterification of Steroidal Lactams

In a round-bottom flask, 1 mmol of the acid were diluted in 3.3 mL of dry benzene. 2,4,6-Trichlorobenzoyl chloride (1.2 mmol) and triethylamine (2.4 mmol) were added and the mixture refluxed under Ar for 1 h. To this mixture a solution of the steroidal alcohol 50 mg (1 mmol) in 3.3 mL dry benzene and a catalytic amount of 4-dimethylaminopyridine were added. The reflux was continued for 3 h. The benzene was totally removed by evaporation in vacuum and the remaining residue was diluted with CH₂Cl₂. The resulting mixture was extracted with a 5% HCl aqueous solution, the organic layer was washed with a 7% NaHCO₃ aqueous solution and finally with water, dried over Na₂SO₄ and the solvent was removed under reduced pressure. The residue was chromatographed by flash column chromatography on silica gel.

General Procedure C for the Esterification of Steroidal Lactams

A mixture of alcohol (1 mmol), Et₃N (1.3 mmol) and a catalytic amount of DMAP was dissolved in CH₂Cl₂ (5 mL) followed by the addition of benzoyl chloride (0.12 mL, 1.1 mmol). The reaction was monitored by TLC and stirred at room temperature for 24 h then taken up with CH₂Cl₂ and quenched with saturated aq NH₄Cl. The organic layer was dried and the crude product was purified by flash column chromatography on silica gel.

The following examples are illustrative of the invention.

Example 1

Scheme 1

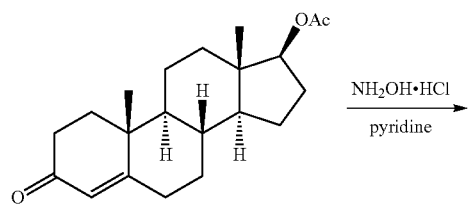

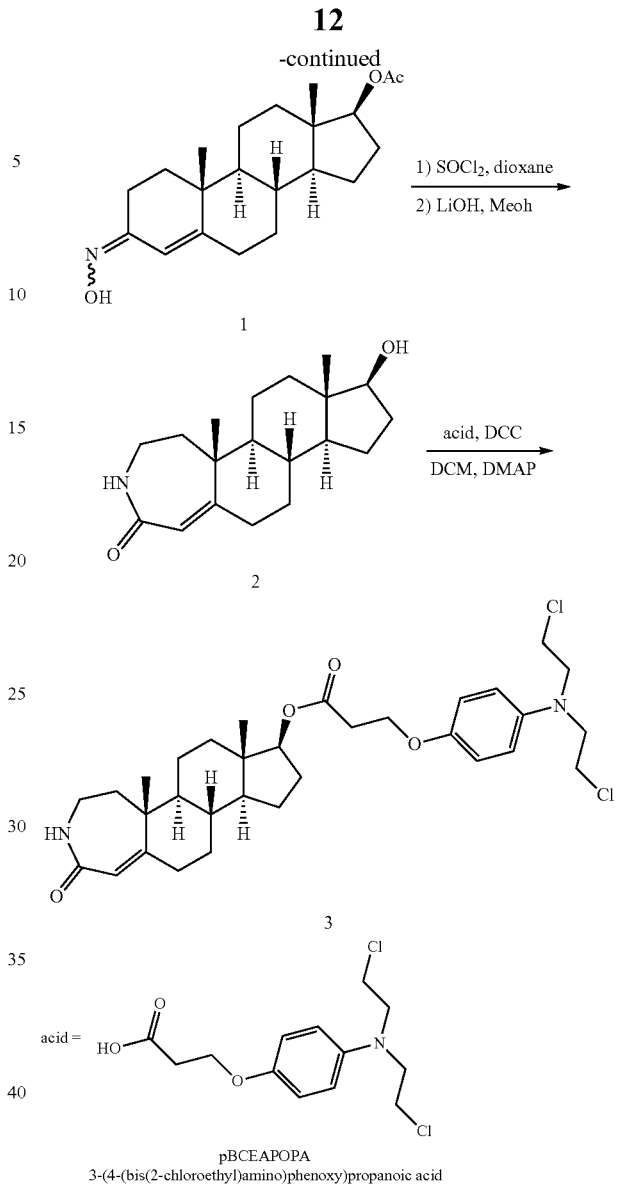

1: 3-Aza-17β-hydroxy-A-homo-4α-androsten-4-one was synthesized by modification (Camoutsis C and Catsoulacos P, J Heterocycl Chem, 1983, 20 (4):1093-4) procedure in three steps from testosterone 17-β-acetate. Testosterone 17-β-acetate (914 mg, 2.77 mmol) was dissolved in 10 ml of dry pyridine. Hydroxylamine hydrochloride (461 mg, 6.64 mmol) was added and the solution was stirred under reflux for 6 h. The solution was poured into water, and the mixture was extracted with ethyl acetate (3×30 mL). The organic layers were dried (Na₂SO₄) and concentrated under reduced pressure to afford the crude product that was further purified by chromatography on SiO₂ (eluent; hexane-ethyl acetate=4/1) to afford 675 mg of the syn- and anti-oximes (74%) as white solids.

2: Syn- and anti-testosterone-17-acetate oximes (100 mg, 0.145 mmol) were dissolved in 3.5 mL of dry dioxane. The mixture was cooled to 0° C. and thionyl chloride (0.6 mL) was added dropwise. The mixture was allowed to reach room temperature and stirred for 3 h. The reaction was quenched with NaHCO₃ and the mixture was extracted with ethyl acetate (3×20 mL). The organic layers were dried (Na₂SO₄) and concentrated under reduced pressure to afford the crude product that was further purified by chromatography on SiO$_2$ (ethyl acetate) to afford 63 mg of 3-aza-17β-acetoxy-A-homo-4α-androsten-4-one (63%) as white solid. 3-Aza-17β-acetoxy-A-homo-4α-androsten-4-one, 1 was dissolved in 4.9 mL MeOH and LiOH (1N, 2 mL) were added dropwise. The mixture was stirred at room temperature for 2 h. The reaction was quenched with NH$_4$Cl and the mixture was extracted with dichloromethane (3×10 mL). The organic layers were dried (Na$_2$SO$_4$) and concentrated under reduced pressure to afford 87 mg of 3-aza-17β-hydroxy-A-homo-4α-androsten-4-one 2 in 74% yield.

3: 3-Aza-17β-hydroxy-A-homo-4α-androsten-4-one 2 was dissolved in 28 mL of dry dichloromethane. Then, 3-(4-(bis(2-chloroethyl)amino)phenoxy)propanoic acid (106 mg, 0.573 mmol), DCC (119 mg, 0.574 mmol) and a catalytic amount of DMAP were added. After the resulting solution was stirred at room temperature for 24 h the solvent was evaporated and the residue was purified by flash column chromatography on silica gel (eluent; hexane-ethyl acetate=1/2) to give conjugate 3 (191 mg, 99%). 3: mp=53-56° C.; [α]$_D^{23}$+10.5 (c=0.91 CHCl$_3$); $^1$H NMR (500 MHz, cdcl$_3$) δ 6.92 (s, 1H), 6.83 (d, J=8.8 Hz, 2H), 6.66 (d, J=8.6 Hz, 2H), 5.72 (s, 1H), 4.66 (t, J=8.4 Hz, 1H), 4.17 (t, J=6.0 Hz, 2H), 3.63 (m, 4H), 3.59 (m, 4H), 3.32-3.04 (m, 2H), 2.75 (t, J=6.1 Hz, 2H), 2.48 (m, 1H), 2.27 (m, 1H), 2.15 (m, 2H), 1.50-1.98 (m, 10H), 1.33 (m, 2H), 1.14 (s, 3H), 1.05 (m, 1H), 0.80 (s, 3H); $^{13}$C NMR (126 MHz, cdcl$_3$) δ 171.0, 170.4, 161.3, 151.3, 140.8, 118.8, 116.3, 114.4, 82.7, 64.4, 54.2, 53.2, 50.2, 44.5, 42.7, 41.9, 40.7, 36.7, 36.2, 35.3, 33.8, 33.1, 27.5, 25.6, 24.9, 23.4, 21.3, 12.1; FT-IR: 3450, 2925, 1731, 1651, 1607, 1512, 1469, 1353, 1238, 1181, 1041, 869, 813.

Example 2

Scheme 2

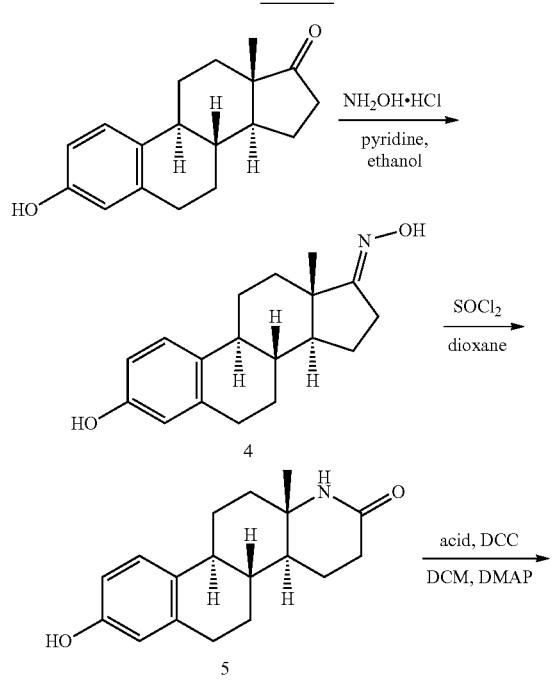

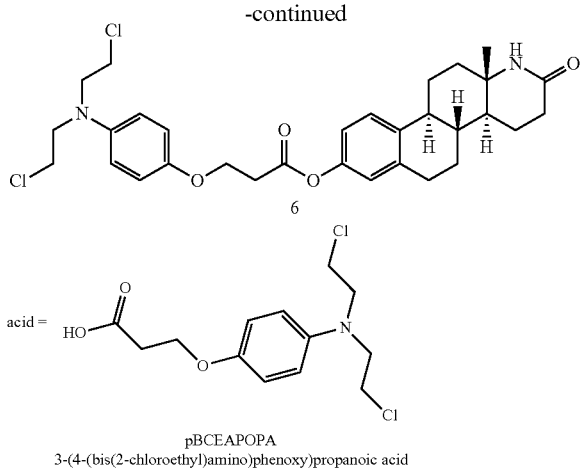

pBCEAPOPA
3-(4-(bis(2-chloroethyl)amino)phenoxy)propanoic acid

4: Estrone oxime was synthesized according to previously described procedure (Ivanenko T I et al, Pharm Chem J, 1982, 16(10):751-6). To a solution of estrone (100 mg, 0.37 mmol) in 2.2 mL absolute ethanol was added hydroxylamine hydrochloride (62 mg, 0.88 mmol) and pyridine (1.2 mL). The mixture was refluxed for 6 hours. Then water was added and the mixture was extracted with ethyl acetate (3×10 mL). The organic layers were dried (Na$_2$SO$_4$) and concentrated under reduced pressure to afford the crude product that was further purified by chromatography on SiO$_2$ (eluent; hexane: ethyl acetate=3:1) to afford 105 mg of estrone oxime (100%) as white solid.

5: Lactam 5 was synthesized according to previously described procedure (Regan B M and Newton Hayes F, J Am Chem Soc, 1956, 78(3): 639-43). Estrone oxime (108 mg, 0.376 mmol) were dissolved in 6.3 mL of dry dioxane. The mixture was cooled to 0° C. and thionyl chloride (0.7 mL) was added dropwise. The mixture was allowed to reach room temperature and stirred for 24 h. The reaction was quenched with NaHCO$_3$ and the mixture was extracted with dichloromethane (3×20 mL). The organic layers were dried (Na$_2$SO$_4$) and concentrated under reduced pressure to afford the crude product that was further purified by chromatography on SiO$_2$ (eluent; hexane:ethyl acetate=2:1) to afford 42 mg of lactam 5 (56% based on recovered starting material) accompanied by recovered starting material [32 mg of starting material (0.112 mmol)].

6: Lactam 5 was dissolved in 14 mL of dry DMF. Then, 3-(4-(bis(2-chloroethyl)amino) phenoxy)propanoic acid (90 mg, 0.293 mmol), DCC (61 mg, 0.293 mmol) and a catalytic amount of DMAP were added. After the resulting solution was stirred at room temperature for 24 h the solvent was evaporated and the residue was purified by flash column chromatography on silica gel (eluent; dichloromethane/acetone=2/1) to give conjugate 6 (56 mg, 68%). Conjugate 6: [α]$_D^{23}$+73.5 (c=0.90 CHCl$_3$); $^1$H NMR (500 MHz, CDCl$_3$) δ 7.25 (d, J=6.0 Hz, 1H), 6.89 (d, J=8.8 Hz, 2H), 6.82 (s, 1H), 6.68 (d, J=8.8 Hz, 2H), 6.31 (s, 1H), 4.30 (t, J=6.1 Hz, 2H), 3.62 (dt, J=29.2, 6.6 Hz, 8H), 2.97 (dd, J=15.1, 9.0 Hz, 2H), 2.88 (m, 2H), 2.58-2.36 (m, 4H), 2.23-2.00 (m, 2H), 1.92-1.66 (m, 3H), 1.60-1.29 (m, 4H), 1.19 (s, 3H); $^{13}$C NMR (126 MHz, CDCl$_3$) δ 171.7, 169.8, 151.3, 148.5, 141.0, 137.8, 137.2, 126.1, 121.3, 118.7, 116.5, 114.5, 64.4, 54.4, 54.2, 46.6, 43.4, 40.7, 39.9, 38.9, 34.9, 30.5, 29.5, 26.5, 25.9, 22.1, 19.8; FTIR: 3329, 2927, 2850, 1757, 1626, 1577, 1512, 1437, 1311, 1244, 1157, 1088, 1045, 892.

Example 3

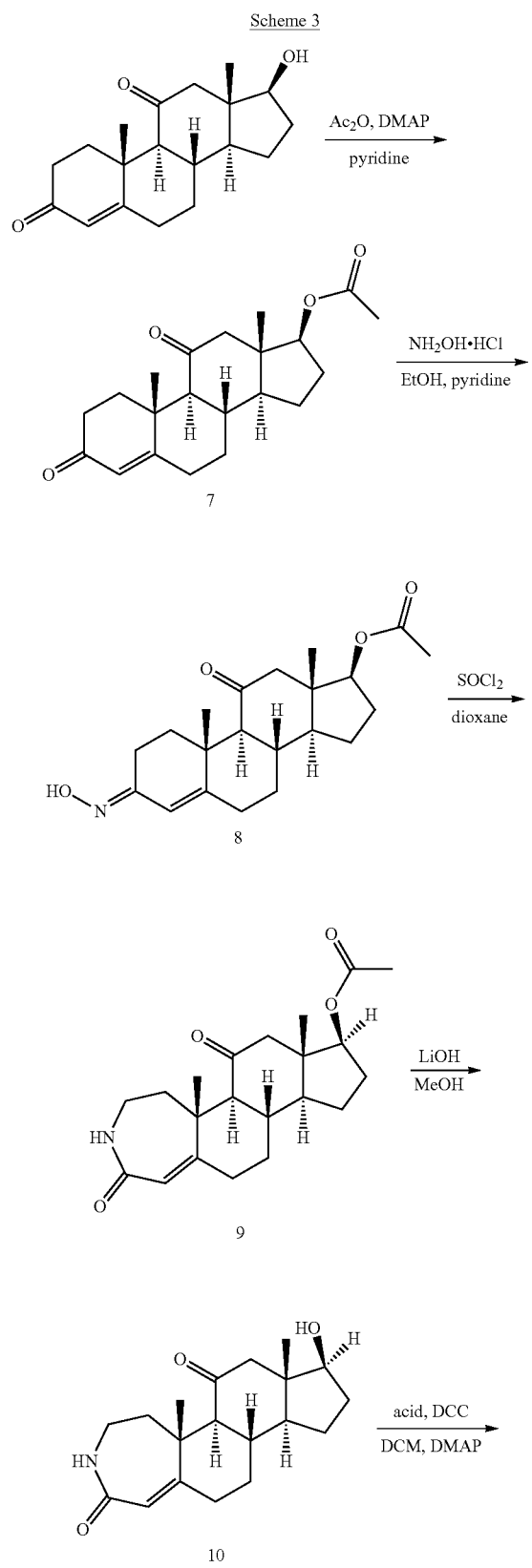

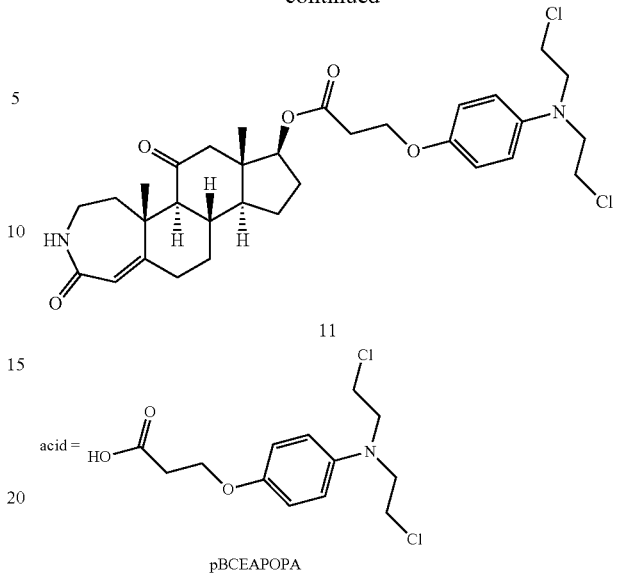

pBCEAPOPA

7: 17-Hydroxyandrost-4-ene-3,11-dione (484 mg, 1.59 mmol) was dissolved in 2.2 mL acetic anhydride. Then, 4 mg (0.037 mmol) of DMAP and 0.25 mL of dry pyridine were added. The mixture was stirred at room temperature for 24 h. The reaction was quenched with water and the mixture was extracted with ethyl acetate (3×30 mL). The organic layers were dried ($Na_2SO_4$) and concentrated under reduced pressure to afford the crude product that was further purified by chromatography on $SiO_2$ (eluent; hexane:ethyl acetate=6:1) to afford 472 mg of 17-acetoxyandrost-4-ene-3,11-dione in 86% yield. 7: mp=162-164° C. $[\alpha]_D^{23}$+148.0 (c 1.68 $CHCl_3$); $^1$H NMR (500 MHz, cdcl$_3$) δ 5.69 (s, 1H), 4.76 (t, J=8.6 Hz, 1H), 2.83-2.69 (m, 1H), 2.54-2.20 (m, 6H), 2.01 (d, J=1.2 Hz, 3H), 1.92 (m, 3H), 1.85-1.55 (m, 4H), 1.51-1.41 (m, 1H), 1.44-1.34 (m, 3H), 1.32-1.10 (m, 2H), 0.85-0.69 (m, 3H); $^{13}$C NMR (126 MHz, cdcl$_3$) δ 208.3, 199.5, 170.8, 168.3, 124.6, 80.2, 62.6, 54.8, 49.4, 46.2, 38.2, 37.0, 34.7, 33.7, 32.1, 31.7, 27.6, 22.9, 20.9, 17.2, 12.8; FT-IR: 3443, 2958, 2935, 2850, 1732, 1702, 1677, 1618, 1426, 1373, 1360, 1343, 1271, 1238, 1224, 1045, 1027

8: To a solution of 17-acetoxyandrost-4-ene-3,11-dione (465 mg, 1.35 mmol) in 7 mL absolute ethanol was added hydroxylamine hydrochloride (100 mg, 1.44 mmol) and dry pyridine (4.2 mL). The mixture was stirred at room temperature for 24 hours. Then, water was added and the mixture was extracted with ethyl acetate (3×40 mL). The organic layers were dried ($Na_2SO_4$) and concentrated under reduced pressure to afford the crude product that was further purified by chromatography on $SiO_2$ (eluent; dichloromethane:ethyl acetate=20:1) to afford 461 mg of the oximes 8 (95%).

9: Oxime 8 (264 mg, 0.74 mmol) were dissolved in 13 mL of dry dioxane. The mixture was cooled to 0° C. and thionyl chloride (1.4 mL) was added dropwise. The mixture was allowed to reach room temperature and stirred for 24 h. The reaction was quenched with $NaHCO_3$ and the mixture was extracted with ethyl acetate (3×20 mL). The organic layers were dried ($Na_2SO_4$) and concentrated under reduced pressure to afford the crude product that was further purified by chromatography on $SiO_2$ (eluent; ethyl acetate:methanol=1:0.03) to afford 163 mg of lactam 9 in 62% yield. 9: $^1$H NMR (500 MHz, cdcl$_3$) δ 6.39 (s, 1H), 5.75 (s, 1H), 4.78 (t, J=8.6

Hz, 1H), 3.35-3.18 (m, 1H), 3.09 (dt, J=14.7, 7.2 Hz, 1H), 2.67 (dd, J=14.9, 8.2 Hz, 1H), 2.48 (td, J=13.6, 3.9 Hz, 1H), 2.34-2.20 (m, 3H), 2.14 (dd, J=9.3, 6.5 Hz, 1H), 2.03 (s, 3H), 2.01-1.86 (m, 2H), 1.83-1.53 (m, 5H), 1.48-1.37 (m, 1H), 1.38 (s, 3H), 1.28-1.08 (m, 1H), 0.76 (s, 3H); $^{13}$C NMR (126 MHz, cdcl$_3$) δ 209.0, 170.8, 169.5, 158.4, 120.1, 80.1, 62.4, 55.1, 49.9, 46.7, 43.6, 40.4, 36.8, 36.8, 35.5, 33.2, 27.6, 22.8, 21.1, 20.9, 12.8; FT-IR: 3428, 2971, 2920, 2878, 2364, 2341, 1736, 1701, 1664, 1639, 1599, 1444, 1375, 1339, 1245, 1127, 1089, 1046.

10: Lactam 9 76 mg (0.21 mmol) was dissolved in 3 mL MeOH and LiOH (1N, 1.2 mL) were added dropwise. The mixture was stirred at room temperature for 1 h. The reaction was quenched with NH$_4$Cl and the mixture was extracted with dichloromethane (3×5 mL). The organic layers were dried (Na$_2$SO$_4$) and concentrated under reduced pressure to afford 67 mg of lactam 10. 10: $^1$H NMR (500 MHz, dmso) δ 7.72 (s, 1H), 5.51 (s, 1H), 4.66 (d, J=4.7 Hz, 1H), 3.66 (dd, J=13.4, 8.4 Hz, 1H), 3.08-2.90 (m, 2H), 2.47-2.32 (m, 2H), 2.29 (d, J=11.5 Hz, 1H), 2.21 (d, J=11.2 Hz, 1H), 2.14-2.01 (m, 2H), 2.01-1.78 (m, 3H), 1.74-1.50 (m, 3H), 1.40 (m, 1H), 1.28 (s, 3H), 1.23 (s, 1H), 1.15-1.02 (m, 1H), 0.55 (s, 3H); $^{13}$C NMR (126 MHz, dmso) δ 210.2, 167.8, 157.3, 120.3, 78.1, 61.0, 54.5, 48.8, 47.1, 43.1, 40.4, 36.8, 35.5, 34.9, 33.1, 29.9, 22.3, 20.9, 11.8; FT-IR: 3423, 3262, 2952, 2923, 2853, 1693, 1647, 1609, 1458, 1407, 1375, 1353, 1261, 1062.

11: Lactam 10 was dissolved in 8.2 mL of dry DCM. Then, 3-(4-(bis(2-chloroethyl)amino)phenoxy)propanoic acid (51 mg, 0.17 mmol), DCC (51 mg, 0.25 mmol) and a catalytic amount of DMAP were added. After the resulting solution was stirred at room temperature for 24 h the solvent was evaporated and the residue was purified by flash column chromatography on silica gel (eluent; ethyl acetate) to give conjugate 11 (48.5 mg, 96%). Conjugate 11: $^1$H NMR (500 MHz, cdcl$_3$) δ 6.83 (d, J=9.0 Hz, 2H), 6.67 (d, J=9.0 Hz, 2H), 6.11 (s, 1H), 5.76 (s, 1H), 4.86 (t, J=8.6 Hz, 1H), 4.17 (t, J=6.2 Hz, 2H), 3.61 (m, 8H), 3.25 (m, 1H), 3.18-3.01 (m, 1H), 2.84-2.59 (m, 2H), 2.59-2.38 (m, 1H), 2.37-2.25 (m, 3H), 2.16 (m, 1H), 2.10-1.89 (m, 3H), 1.87-1.55 (m, 4H), 1.39 (s, 3H), 1.26 (m, 2H), 1.12 (m, 1H), 0.76 (s, 3H); $^{13}$C NMR (126 MHz, cdcl$_3$) δ 208.9, 170.9, 169.5, 158.7, 151.3, 140.9, 119.9, 116.2, 114.5, 80.4, 64.2, 62.4, 55.1, 54.3, 49.9, 46.8, 43.6, 40.7, 36.8, 35.5, 34.9, 33.9, 27.6, 25.6, 24.9, 22.8, 21.2, 12.8; FT-IR: 3432, 3328, 2927, 2850, 1733, 1701, 1664, 1626, 1599, 1513, 1444, 1389, 1369, 1310, 1273, 1243, 1179, 1087, 1041, 999.

Example 4

Scheme 4

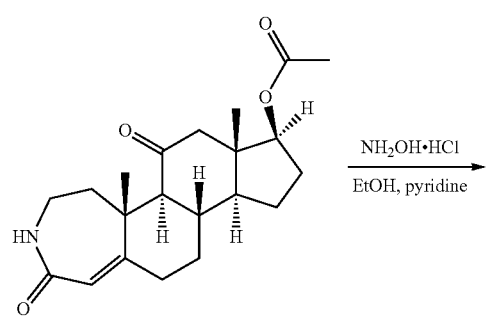

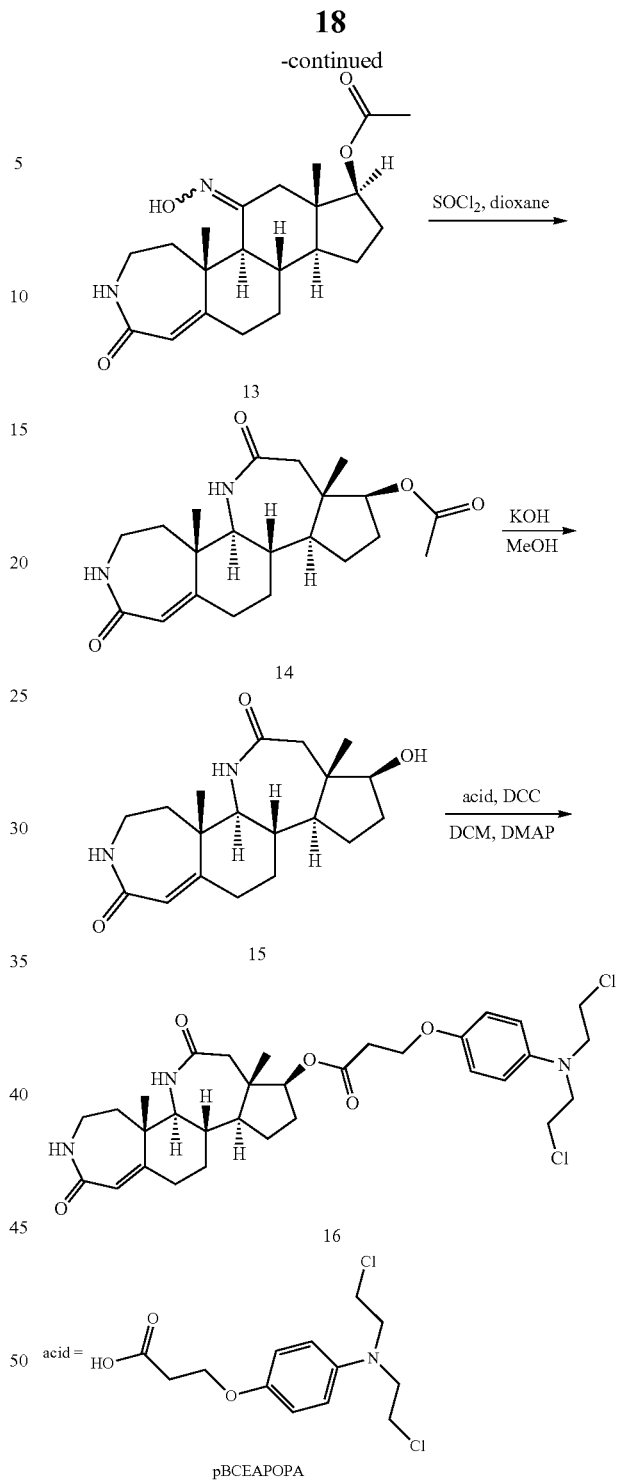

13: To a solution of 12 (100 mg, 0.28 mmol) in 1.5 mL absolute ethanol in a sealed tube was added hydroxylamine hydrochloride (21 mg, 0.31 mmol) and dry pyridine (0.9 mL). The mixture was heated at 140° C. for 7 days. Then, water was added and the mixture was extracted with ethyl acetate (3×5 mL). The organic layers were dried (Na$_2$SO$_4$) and concentrated under reduced pressure to afford a crude product, which was used to the next step without further purification.

14: The crude oximes 13 described above (0.28 mmol) were dissolved in 4.9 mL of dry dioxane. The mixture was cooled to 0° C. and thionyl chloride (0.54 mL) was added dropwise. The mixture was allowed to reach room temperature and stirred for 24 h. The reaction was quenched with NaHCO$_3$ and the mixture was extracted with ethyl acetate (3×20 mL). The organic layers were dried (Na$_2$SO$_4$) and concentrated under reduced pressure to afford the crude product that was further purified by chromatography on SiO$_2$ (eluent; ethyl acetate:methanol=1: 0.1) to afford 52 mg of lactam in 50% yield. 14: $^1$H NMR (500 MHz, cdcl$_3$) δ 7.00 (s, 1H), 5.77 (s, 1H), 5.59 (s, 1H), 4.61 (t, J=8.3 Hz, 1H), 3.20 (m, 2H), 3.02 (dd, J=9.6, 5.0 Hz, 1H), 2.48-2.40 (m, 2H), 2.31 (d, J=13.7 Hz, 1H), 2.16 (m, 2H), 2.09-2.0-1.97 (m, 5H), 1.74-1.84 (m, 2H), 1.51-1.40 (m, 2H), 1.35-1.30 (m, 1H), 1.24 (s, 3H), 1.23 (m, 1H), 1.08 (m, 1H), 0.95 (s, 3H); $^{13}$C NMR (126 MHz, cdcl$_3$) δ 175.1, 170.9, 169.4, 156.3, 120.4, 80.1, 64.2, 55.5, 45.2, 44.6, 41.0, 40.8, 38.0, 36.3, 34.4, 31.0, 25.4, 25.2, 21.9, 21.0, 11.7.

15: Lactam 14 28 mg (0.084 mmol) was dissolved in 1.2 mL MeOH and LiOH (1N, 0.5 mL) were added dropwise. The mixture was stirred at room temperature for 1 h. The reaction was quenched with NH$_4$Cl and the mixture was extracted with ethylacetate (3×5 mL). The organic layers were dried (Na$_2$SO$_4$) and concentrated under reduced pressure. The crude product that was further purified by chromatography on SiO$_2$ (eluent; ethyl acetate:methanol=1: 0.1) to afford 28 mg of lactam 15 in 100% yield. 15: $^1$H NMR (500 MHz, dmso) δ 7.75 (s, 1H), 6.13 (d, J=3.9 Hz, 1H), 5.53 (s, 1H), 4.66 (d, J=5.3 Hz, 1H), 3.40 (m, 2H), 3.11-2.93 (m, 2H), 2.44-2.34 (m, 1H), 2.29 (s, 2H), 2.04-1.72 (m, 5H), 1.65 (m, 2H), 1.24 (m, 3H), 1.20 (s, 3H), 0.89 (m, 1H), 0.66 (s, 3H); $^{13}$C NMR (126 MHz, dmso) δ 174.6, 167.7, 156.1, 120.1, 78.1, 69.8, 63.4, 44.9, 44.2, 41.2, 40.4, 37.7, 35.3, 33.7, 31.3, 27.7, 24.4, 20.9, 10.7.

16: Lactam 15 (30 mg, 0.09 mmol) was dissolved in 9 mL of dry DCM. Then, 3-(4-(bis(2-chloroethyl)amino)phenoxy) propanoic acid (67 mg, 0.22 mmol), DCC (60 mg, 0.29 mmol) and a catalytic amount of DMAP were added. After the resulting solution was stirred at room temperature for 24 h the solvent was evaporated and the residue was purified by flash column chromatography on silica gel (eluent; ethyl acetate/MeOH=10/1) to give conjugate 16 (39 mg, 70%). $^1$H NMR (500 MHz, cdcl$_3$) δ 6.85 (d, J=9.0 Hz, 2H), 6.76 (s, 1H), 6.65 (d, J=9.0 Hz, 2H), 5.79 (s, 1H), 5.46 (s, 1H), 4.68 (t, J=8.3 Hz, 1H), 4.17 (t, J=6.2 Hz, 2H), 3.60 (m, 4H), 3.51-3.42 (m, 1H), 3.18 (m, 2H), 3.02 (dd, J=9.5, 5.0 Hz, 1H), 2.85-2.67 (m, 2H), 2.51 (d, J=13.8 Hz, 1H), 2.44 (dd, J=13.6, 10.1 Hz, 1H), 2.33 (d, J=13.8 Hz, 1H), 2.25-2.06 (m, 2H), 2.07-1.73 (m, 5H), 1.73-1.28 (m, 5H), 1.25 (s, 3H), 1.17-1.03 (m, 2H), 0.96 (s, 3H); $^{13}$C NMR (126 MHz, cdcl$_3$) δ 174.7, 170.9, 169.1, 155.6, 151.3, 140.9, 120.7, 116.3, 114.4, 80.5, 64.2, 64.1, 55.5, 54.2, 45.3, 44.5, 41.1, 40.7, 38.1, 36.3, 34.8, 34.4, 33.9, 31.0, 25.6, 25.5, 25.2, 24.9, 21.9, 11.8. FT-IR: 3410, 3330, 2926, 2850, 1734, 1654, 1627, 1577, 1513, 1445, 1349, 1273, 1243, 1180, 1133, 1110, 1087, 1044, 890.

Example 5

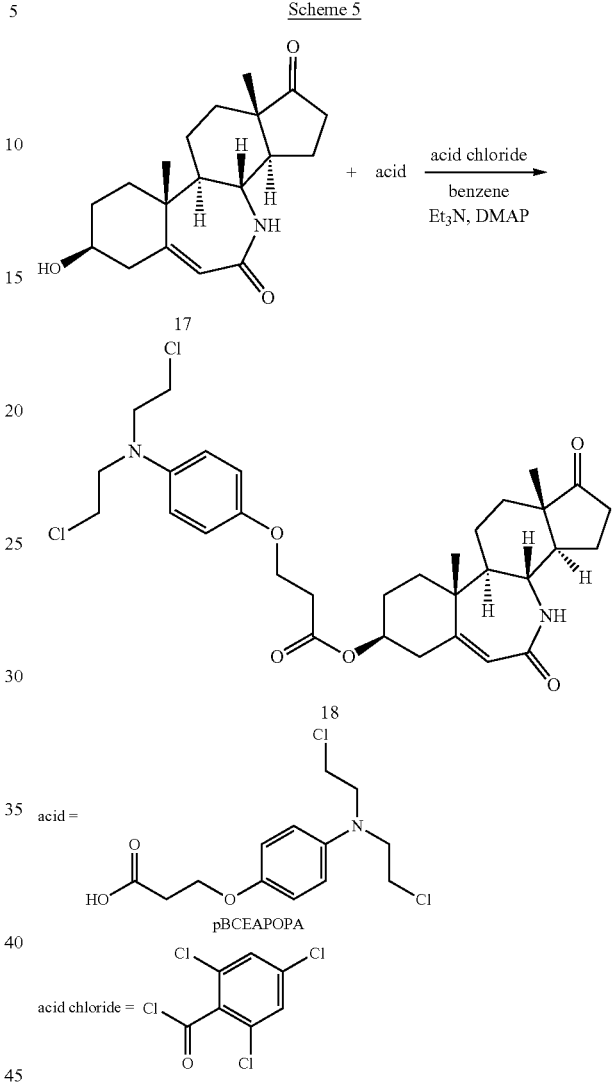

Scheme 5

Lactam 17 was synthesized according to Koutsourea et al (Steroids, 2003, 68(7-8):659-66).

18: In a round-bottom flask 48 mg (0.157 mmol) of the acid were diluted in 0.5 ml of dry benzene. 2,4,6-Trichlorobenzoyl chloride (30 μl, 0.189 mmol) and triethylamine (53 μl, 0.378 mmol) were added and the mixture refluxed under Ar for 1 h. To this mixture a solution of the steroidal alcohol 50 mg (0.157 mmol) in 0.5 ml dry benzene and a catalytic amount of 4-dimethylaminopyridine were added. The reflux was continued for 3 h. The benzene was totally removed by evaporation in vacuum and the remaining residue was diluted with CH$_2$Cl$_2$. The resulting mixture was extracted with a 5% HCl aqueous solution, the organic layer was washed with a 7% NaHCO$_3$ aqueous solution and finally with water, dried over Na$_2$SO$_4$ and the solvent removed under reduced pressure. The residue was chromatographed on a silica gel column (eluent; ethyl acetate/MeOH=100/1) to give 46 mg of conjugate 18 in 48% yield. Conjugate 18: $^1$H NMR (500 MHz, cdcl$_3$) δ 6.84 (d, J=8.5 Hz, 2H), 6.67 (d, J=8.5 Hz, 2H), 5.90 (s, 1H), 5.86 (s, 1H), 4.78 (m, 1H), 4.19 (m, 2H), 3.58-3.59 (m, 8H), 3.48 (m, 1H), 2.61-1.25 (18H), 1.29 (s, 3H), 0.88 (s, 3H); [M+H]+=605.

Example 6

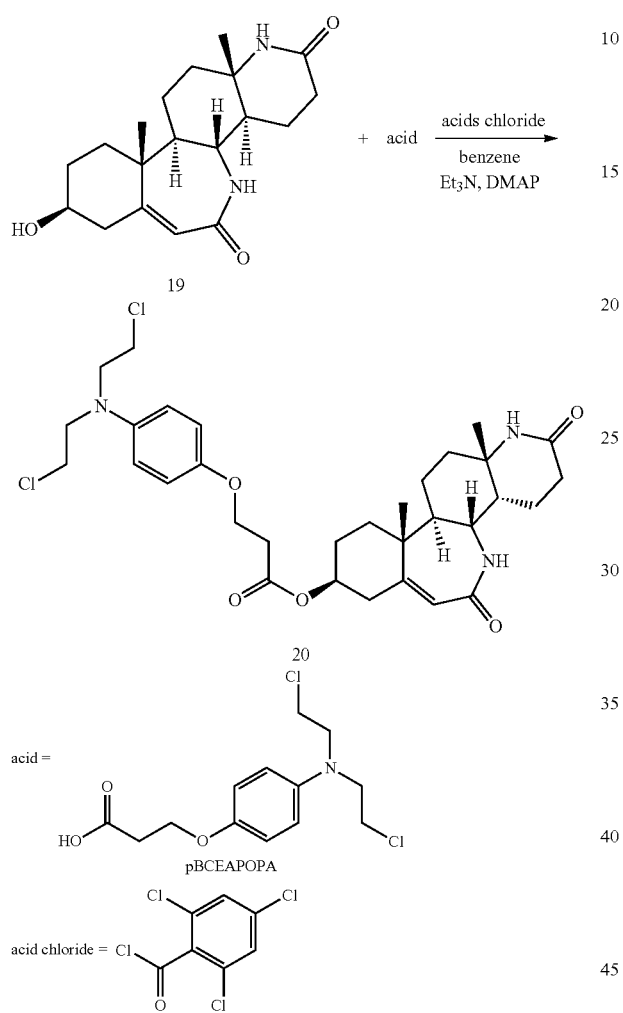

Lactam 19 was synthesized according to Koutsourea et al (Steroids, 2003, 68(7-8):659-66).

20: In a round-bottom flask 46 mg, (0.15 mmol) of the acid were diluted in 0.5 ml of dry benzene. 2,4,6-Trichlorobenzoyl chloride (28 μl, 0.18 mmol) and triethylamine (50 μl, 0.36 mmol) were added and the mixture refluxed under Ar for 1 h. To this mixture a solution of the steroidal alcohol 50 mg (0.150 mmol) in 0.5 ml dry benzene and a catalytic amount of 4-dimethylaminopyridine were added. The reflux was continued for 3 h. The benzene was totally removed by evaporation in vacuum and the remaining residue was diluted with $CH_2Cl_2$. The resulting mixture was extracted with a 5% HCl aqueous solution, the organic layer was washed with a 7% $NaHCO_3$ aqueous solution and finally with water, dried over $Na_2SO_4$ and the solvent removed under reduced pressure. The residue was chromatographed on a silica gel column (eluent; ethyl acetate/MeOH=100/2) to give 19 mg of conjugate 20 in 20% yield. 20: $^1$H NMR (500 MHz, cdcl$_3$) δ 7.18 (s, 1H), 6.84 (d, J=8.5 Hz, 2H), 6.65

(d, J=8.5 Hz, 2H), 6.60 (s, 1H), 5.82 (s, 1H), 4.80 (1H, m), 4.21 (2H, m), 3.50 (m, 8H), 3.20 (1H, m), 2.80-1.30 (19H), 1.20 (s, 3H), 0.9 (s, 3H); [M+H]+=621.

Example 7

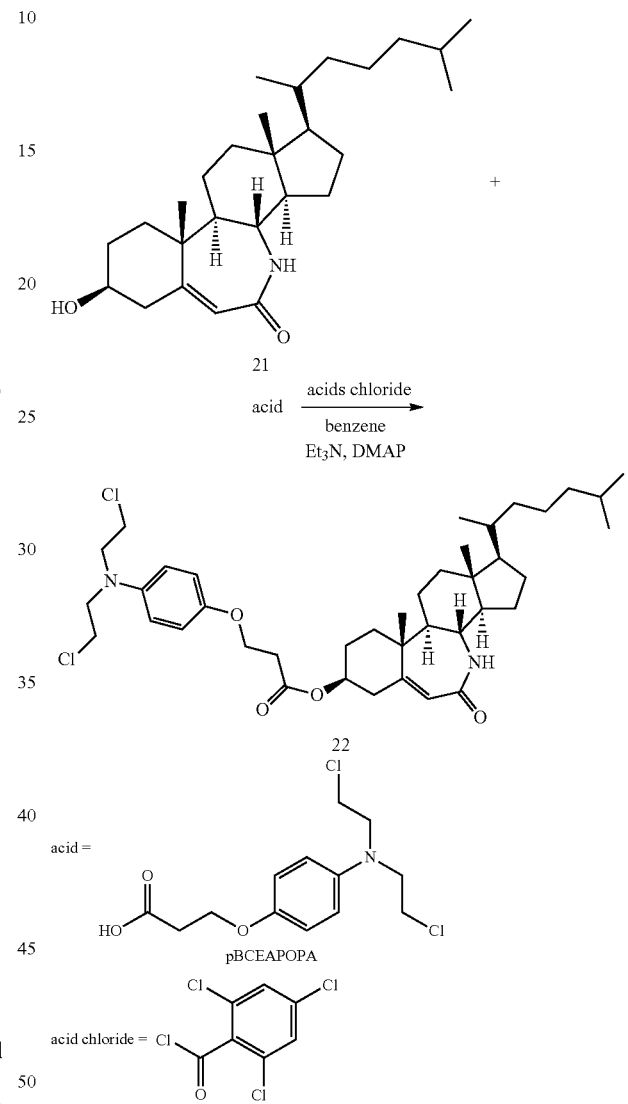

Lactam 21 was synthesized according to Koutsourea et al (Steroids, 2003, 68(7-8):659-66).

22: In a round-bottom flask 37 mg, (0.12 mmol) of the acid were diluted in 0.4 ml of dry benzene. 2,4,6-Trichlorobenzoyl chloride (22 μl, 0.144 mmol) and triethylamine (40 μl, 0.288 mmol) were added and the mixture refluxed under Ar for 1 h. To this mixture a solution of the steroidal alcohol 50 mg (0.120 mmol) in 0.4 ml dry benzene and a catalytic amount of 4-dimethylaminopyridine were added. The reflux was continued for 3 h. The benzene was totally removed by evaporation in vacuum and the remaining residue was diluted with $CH_2Cl_2$. The resulting mixture was extracted with a 5% HCl aqueous solution, the organic layer was washed with a 7% $NaHCO_3$ aqueous solution and finally with water, dried over $Na_2SO_4$ and the solvent removed under reduced pressure. The residue was chromatographed on a silica gel column (eluent; ethyl acetate) to give 34 mg of conjugate 22 in 40% yield. 22: $^1$H NMR (500 MHz, cdcl$_3$) δ 6.84 (d, J=8.5 Hz, 2H), 6.60 (d, J=8.5 Hz, 2H), 5.90 (s, 1H), 5.79 (s, 1H), 4.80 (m 1H), 4.15 (m, 2H), 3.5 (m, 8H), 3.25 (m, 1H), 2.8-0.8 (22H); [M+H]$^+$=605.

Example 8

In Vitro and In Vivo Biological Testing for Anticancer Activity

A) In Vitro Anticancer Activity

Nine well established human cancer cell lines (table 1) were treated for testing cytostatic and cytotoxic activity produced by the newly synthesized compounds. The cell lines were obtained from the American Type Culture Collection (ATCC) and were grown in different culture medium according to the instructions. The MTT ((3-(4, 5-imethyl-thiazol-2-yl)-2, 5-diphenyltetrazolium bromide) assay is a well-established and standard method for evaluating the cytostatic and cytotoxic activity of drugs and chemicals (Trafalis D T et al, J BUON, 2003, 8:333-9; Trafalis D T et al, J BUON, 2004, 9(3):275-82; Trafalis D T et al, J BUON, 2005; 10:227-34; Trafalis D T et al, Breast Cancer Res Treat, 2006, 97:17-31). Briefly, the cells were plated in 96-well plate at a density of ~3×10$^4$ cells/ml per well and maintained for 72 h at 37° C. in a 5% CO2 incubator and grown as monolayers or suspensions. After 24 hours, cells were treated with 0.1-100 μmol/l of the compounds for 48 h. The viability of cultured cells was estimated MTT (Sigma, St Louis, Mo., USA) metabolic assay as described previously. Absorbance of the converted dye was measured at a wavelength of 540 nm on an ELISA reader (Versamax, Orleans, USA). The mean concentrations of each drug that generated 50% or total (100%) growth inhibition (GI50 and TGI, respectively) as well as the drug concentrations that produced cytotoxicity against 50% of the cultured cells [(half maximal cytotoxic concentration (IC50)] were calculated using the linear regression method. Using seven absorbance measurements [time 24 h (Ct24), control growth 72 h (Ct72), and test growth in the presence of drug at five concentration levels (Tt72x)], the percentage of growth was calculated at each level of the drug concentrations. The percentage growth inhibition was calculated according to National Cancer Institute (NCI) as: [(Tt72x)−(Ct24)/(Ct72)−(Ct24)]×100 for concentrations for which Tt72x>Ct24 and [(Tt72x)−(Ct24)/Ct24]×100 for concentrations for which Tt72x<Ct24; GI50 was calculated from [(Tt72x)−(Ct24)/(Ct72)−(Ct24)]×100=50, TGI from [(Tt72x)−(Ct24)/(Ct72)−(Ct24)]×100=0, and IC50 from [(Tt72x)−(Ct24)/Ct24]×100=50. All the experiments were carried out in triplicate.

TABLE 1

| Cancer Type | Human Cell line designation | Oncogenes | Special Characteristics |
| --- | --- | --- | --- |
| Ovarian Adenocarcinoma | SK-OV-3 (SKOV-3) | | Tumor Necrosis Factor; Diphtheria Toxin; Cis-platinum and Adriamycin resistant |
| Epithelial Ovarian Adenocarcinoma | NIH:OVCAR-3 | | Androgen/Estrogen/Progesterone receptor positive; Adriamycin, Melphalan and Cisplatin resistant |
| Ovarian Carcinoma | UWB1.289 | p53+ BRCA1− (mutated) | Estrogen/Progesterone receptor negative |
| Ovarian Carcinoma | UWB1.289 + BRCA1 | p53+ BRCA1+ | Estrogen/Progesterone receptor negative |
| Epithelial Breast Adenocarcinoma | MCF7 | WNT7B+ | Estrogen receptor positive Insulin-like growth factor binding proteins (IGFBP) BP-2; BP-4; BP-5 |
| Epithelial Breast Adenocarcinoma | T-47D | WNT7B+ | calcitonin; androgen receptor, positive; progesterone receptor, positive; glucocorticoid; prolactin; estrogen receptor, positive |
| Prostate Adenocarcinoma | PC-3 | | Hormone resistant |
| Acute T-lymphoblastic leukemia | MOLT-4 | | Terminal deoxynucleotidyl transferase (TdT) expressed |
| Chronic myelogenous leukemia | K-562 | | |

The results of in vitro cytostatic (GI50, TGI) and cytotoxic (IC50) effects induced by the tested compounds against human cancer cell lines are presented on Tables 2, 3, 4.

TABLE 2

| HUMAN CANCER CELL LINES | Compounds | | | | | | | | |
|---|---|---|---|---|---|---|---|---|---|
| | pBCEAPOPA | | | ASE | | | 22 | | |
| | GI50 | TGI | IC50 | GI50 | TGI | IC50 | GI50 | TGI | IC50 |
| UWB1.289 | 20 | 76 | >100 | 16 | 30 | 54 | 80 | >100 | >100 |
| UWB1.289 + BRCA1 | >100 | >100 | >100 | 80 | >100 | >100 | >100 | >100 | >100 |
| OVCAR-3 | 56 | 92 | >100 | 36 | 52 | 64 | >100 | >100 | >100 |
| SKOV-3 | 50 | >100 | >100 | 45 | 92 | >100 | >100 | >100 | >100 |
| MCF-7 | >100 | >100 | >100 | 29 | 57 | 96 | >100 | >100 | >100 |
| T-47D | 95 | >100 | >100 | 22 | 47 | 92 | 85 | >100 | >100 |
| PC-3 | 89 | >100 | >100 | 34 | 49 | 89 | 90 | >100 | >100 |
| MOLT-4 | 31 | 75 | >100 | 8 | 56 | 93 | 22 | 63 | >100 |
| K-562 | 46 | 91 | >100 | 9 | 78 | >100 | 36 | 94 | >100 |

TABLE 3

| HUMAN CANCER CELL LINES | Compounds | | | | | | | | |
|---|---|---|---|---|---|---|---|---|---|
| | 18 | | | 20 | | | 6 | | |
| | GI50 | TGI | IC50 | GI50 | TGI | IC50 | GI50 | TGI | IC50 |
| UWB1.289 | 13 | 42 | 70 | 9 | 36 | 76 | 6 | 20 | 44 |
| UWB1.289 + BRCA1 | 20 | 38 | 69 | 30 | 76 | >100 | 18 | 66 | 88 |
| OVCAR-3 | 20 | 47 | 70 | 54 | 82 | >100 | 30 | 40 | 56 |
| SKOV-3 | 24 | 46 | 68 | 42 | 78 | >100 | 12 | 76 | >100 |
| MCF-7 | 21 | 46 | 79 | 25 | 68 | >100 | 15 | 36 | 65 |
| T-47D | 14 | 32 | 72 | 26 | 59 | 98 | 10 | 30 | 55 |
| PC-3 | 23 | 36 | 70 | 29 | 44 | 68 | 16 | 29 | 51 |
| MOLT-4 | 5 | 38 | 76 | 11 | 46 | 85 | 5 | 28 | 50 |
| K-562 | 6 | 38 | 87 | 13 | 49 | 90 | 5 | 30 | 50 |

TABLE 4

| HUMAN CANCER CELL LINES | Compounds | | | | | | | | |
|---|---|---|---|---|---|---|---|---|---|
| | 3 | | | 11 | | | 16 | | |
| | GI50 | TGI | IC50 | GI50 | TGI | IC50 | GI50 | TGI | IC50 |
| UWB1.289 | 3 | 8 | 20 | 6 | 20 | 25 | 3 | 28 | 40 |
| UWB1.289 + BRCA1 | 12 | 25 | 40 | 22 | 31 | 42 | 12 | 32 | 50 |
| OVCAR-3 | 21 | 32 | 42 | 8 | 18 | 22 | 9 | 20 | 35 |
| SKOV-3 | 18 | 52 | 76 | 20 | 32 | 44 | 20 | 46 | 70 |
| MCF-7 | 17 | 38 | 70 | 25 | 68 | >100 | 15 | 36 | 65 |
| T-47D | 10 | 25 | 66 | 26 | 59 | 98 | 10 | 30 | 55 |
| PC-3 | 22 | 30 | 56 | 29 | 44 | 68 | 16 | 29 | 51 |
| MOLT-4 | 3 | 27 | 65 | 1.5 | 20 | 45 | 4 | 36 | 56 |
| K-562 | 3 | 30 | 71 | 2 | 35 | 55 | 7 | 47 | 65 |

B) In Vivo Acute Toxicity

For intraperitoneal (i.p.) treatment, stock solutions of the tested compounds were prepared immediately before use. They were suspended in corn oil in the desired concentration following initial dissolution in 10% dimethylsulfoxide (DMSO). This concentration by itself produced no observable toxic effect.

C57Bl/6 female mice were used for toxicity studies. Mice obtained from experimental section of the Hellenic Pasteur Institute.

Briefly, the acute toxicity induced by the tested compounds was determined, as previously had very well described (Catsoulacos P et al, Cancer Chemother Pharmacol, 1979, 3(1):67-70; Catsoulacos P et al, J Pharm Sci, 1978, 67(9):1342-3; Catsoulacos P et al, Anticancer Res, 1995; 15:827-30) following a single intraperitoneal (i.p.) injection into groups of ten (10) C57Bl/6 mice at four different dosages; the mice were observed for 30 days and the therapeutic dose of the compounds, which is usually defined as LD10 (lethal dose for 10% of animals) as well as LD50 (lethal dose for 50% of animals) were determined after graphical estimation (30-day curves). The toxicity of the tested compounds was assessed from lethality in C57Bl/6 mice. The LD50 and LD10 values were estimated graphically, where the percentage of deaths due to the toxicity of each dose was shown in the ordinate, while the administered doses were indicated on the abscissa (table 5).

C) In Vivo Antitumor Activity

Experiment was initiated on day 0 by implanting intraperitoneally (i.p.) $10^6$ ascites cells of P388 lymphocytic leukemia according to the protocol of National Cancer Institute (NCI), USA. For i.p. treatment, stock solutions of the tested compounds were prepared immediately before use. The antitumor activity was assessed from the oncostatic parameter T/C %, which means median survival time (MST) of drug-treated animals (T) to saline treated controls (C). According to the NCI (USA), the minimum criterion of activity is T/C higher than 125%. Moreover, the antitumor activity was estimated from the number of long-term survivors (cures: defined as mice alive for 90 days after tumor inoculation) (Golidim A et al, Nat Cancer Inst Monogr, 1980, 55: 25-26; Experimental evaluation of antitumor drugs in the USA and USSR and clinical correlations. National Cancer Institute monograph. 1980; (55): 1-179).

BALB/c scid female mice were used for antitumor evaluation. These animals carry the severe combined immune deficiency mutation (scid) on the BALB/c background, and obtained from NCSR "Demokritos", Institute of Biology. Mice were kept under conditions of constant temperature and humidity, in sterile cages, with water and food. Six mice were included in each group of treatment and eight in the control group. The tested therapeutic dose of the compounds was defined at the respective LD10 (mg/kgr).

TABLE 5

Acute toxicity of the compounds in C57Bl/6. LD50 and LD10 = lethal doses for 50% and 10% of the population of the treated mice.

| COMPOUNDS | LD50 (mg/kg) | LD10 (mg/kg) |
|---|---|---|
| pBCEAPOPA | 20 | 15 |
| ASE | 50 | 30 |
| 3 | 150 | 130 |
| 6 | 100 | 80 |
| 18 | 110 | 85 |
| 20 | 135 | 110 |
| 22 | — | >300 |
| 11 | 130 | 100 |
| 16 | 165 | 140 |

TABLE 6

Antileukemic activity of the tested compounds against murine P388 lymphocytic leukemia in vivo.

| Compounds | Treatment schedule | Dose (LD10) (mg/kg) | MST ± SD (days) | T/C % | Cures |
|---|---|---|---|---|---|
| pBCEAPOPA | Day 1 | 15 (ip) | 19 | 211* | 0/6 |
| ASE | Day 1 | 30 (ip) | 24 | 267* | 0/6 |
| 3 | Day 1 | 130 (ip) | 39 | 433* | 0/6 |
| 6 | Day 1 | 80 (ip) | 36 | 400* | 0/6 |
| 18 | Day 1 | 85 (ip) | 34 | 378* | 0/6 |
| 20 | Day 1 | 110 (ip) | 32 | 356* | 0/6 |
| 11 | Day 1 | 100 (ip) | 56 | 622* | 1/6 |
| 16 | Day 1 | 140 (ip) | 44 | 489* | 0/6 |
| Controls | Day 1 | Saline | 9 ± 1.5 | 100 | 0/8 |

*p < 0.001

BALB/c scid female mice were used for the in vivo antitumor evaluation of the tested compounds against the human ovarian cancer SCOV-3. Suspensions of $3 \times 10^6$ SCOV-3 cancer cells/0.2 ml/mouse were inoculated subcutaneously in the right or left flank of each animal. Mice were kept under conditions of constant temperature and humidity, in sterile cages, with water and food. Ten mice were included in each group of treatment and control. Testing was carried out according to well-established laboratory protocols. The efficacy of the drugs was determined by the mean change of tumor volume of treated animals (T) over the control (C) (T/C %=TI, Tumor Inhibition) and by the increase of median survival time, according to tumor cell kinetics and biological properties. Tumor volumes or weights were calculated as $0.52 \times a^2 \times b$, where a and b are the minor and major tumor axes and data plotted on a semi-logarithmic graph as mean tumor volumes±standard error of the mean (±SEM) versus time after treatment. When tumors reached at a volume of 0.085-0.1 mm³ mice were divided into control and drug treatment groups (10 mice/group), with similar average tumor volumes in each group. The tested compounds were administered i.p. at doses of LD10/4 respectively on days 1, 5 and 9. For evaluation of antitumor effect, (a) the weekly mean tumor weight or mean tumor volume change was determined and tumor inhibition (TI) was calculated by the formula: TI (%)=[1)(TWT)TWZ)/(TWC)TWZ)]×100, where TWT is determined as the tumor weight (mg) or tumor volume (mm³) in treated animals at the time of evaluation, TWZ is determined as the tumor weight (mg) or tumor volume (mm³) at the time of initiation of treatment (zero time or day 1), TWC is determined as the tumor weight (mg) or tumor volume (mm³) in untreated animals (controls) at the time of evaluation, (b) the percentage of survivors (OS %) at Day-70, (c) the percentage of tumor progression free survivors (PFS %) at the day-70. The results are demonstrated on Table 7.

TABLE 7

Antitumor activity of the tested compounds against SCOV-3 human ovarian cancer in vivo.

| Compounds | Treatment schedule | Dose (LD10/4) (mg/kg) | TI % at Day-35 | OS % on Day-70 | PFS % on Day-70 |
|---|---|---|---|---|---|
| pBCEAPOPA | Days 1, 5, 9 | 4 (ip) | 17 | 40 | 0 |
| ASE | Days 1, 5, 9 | 8 (ip) | 34 | 80 | 40 |
| 3 | Days 1, 5, 9 | 32 (ip) | 62 | 100 | 100 |
| 6 | Days 1, 5, 9 | 20 (ip) | 56 | 100 | 100 |
| 18 | Days 1, 5, 9 | 21 (ip) | 44 | 100 | 80 |
| 20 | Days 1, 5, 9 | 28 (ip) | 41 | 100 | 70 |
| 11 | Days 1, 5, 9 | 25 (ip) | 73 | 100 | 100 |
| 16 | Days 1, 5, 9 | 37 (ip) | 55 | 100 | 100 |
| Controls | Days 1, 5, 9 | Saline | 0 | 0 | 0 |

All differences on TI %, OS %, PFS % are significant at levels of p < 0.05-0.001

D) Pharmacological Effects

The new lactam steroidal alkylators induce significant inhibition effect on poly(ADP-ribose) polymerase (PARP1/2) activity showing half maximal inhibitory concentrations (IC50) less than 1.7 μM, better than the well-known PARP1/2 inhibitor the 3-aminobenzamide (3-AB). Moreover, the new lactam steroidal alkylators produce significant changes on the transcription and mRNA expression of PARP1 and PARP2 in a dose and time depended manner, in vitro and in vivo. At first or in lower doses they can induce an increase of the PARP1 and PARP2 mRNA expression which reaches 5-400 folds higher than control values, generating changes on intracellular NAD+ concentrations and cellular ATP depletion, and later or in higher doses they induce a decrease of PARP1 and PARP2 mRNA expression which can reach near to 100%. The new lactam steroidal alkylators produce significant DNA damage comparable with that induced by their alkylating component alone, as was assessed in vitro by Sister Chromatid Exchanges (SCE's) assay and in vivo by producing 8-hydroxy-2'-deoxyguanosine (8-OHdG) adducts in serum or urine, while they generate significantly higher antitumor activity. Furthermore, the new lactam steroidal alkylators inhibit significantly (>60%) the phosphorylation of ERK1/2 and AKT1/2, and consequently the activation of the PI3K and MAPK molecular signaling pathways. For the first time the molecular pharmacological effects of the lactam steroidal alkylators were investigated in depth.

The invention claimed is:

1. A compound of formula (I) or a pharmaceutically acceptable salt thereof

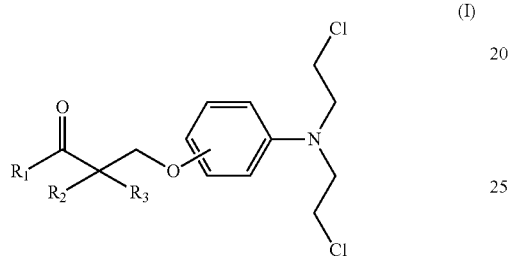

wherein $R_1$ is selected from the group consisting of

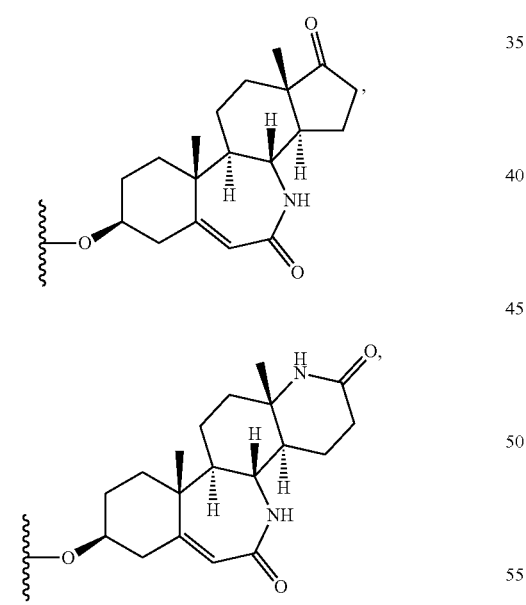

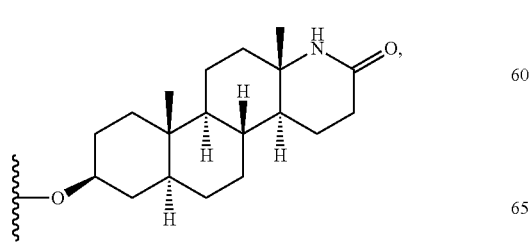

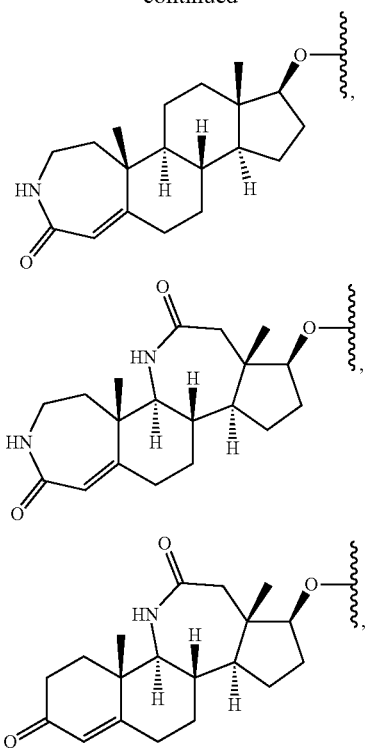

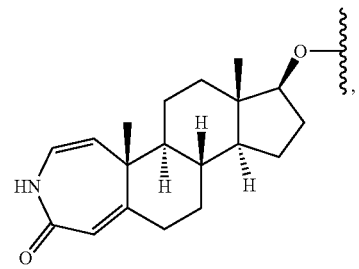

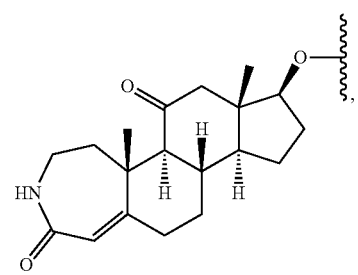

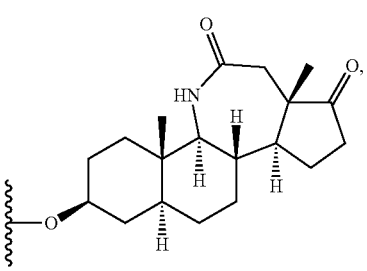

-continued
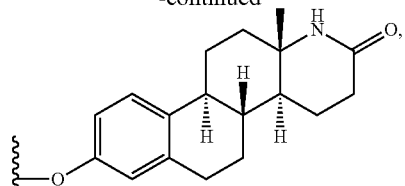
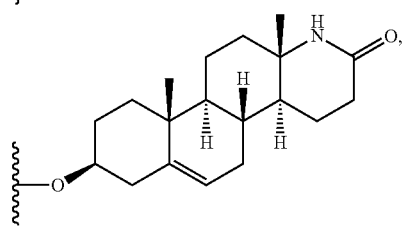
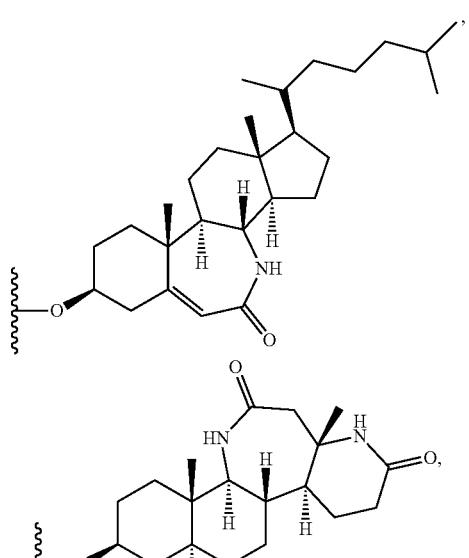
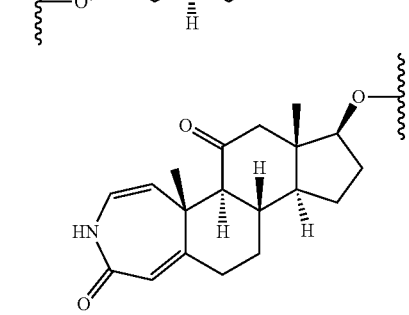
R₂ is selected from the group consisting of H, —CH₃, —CH=CH₂, —CH₂—CH₃, —CH₂CH₂CH₃,
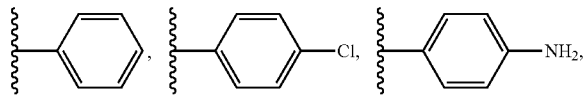
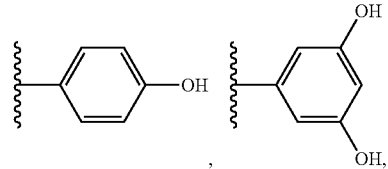
-continued
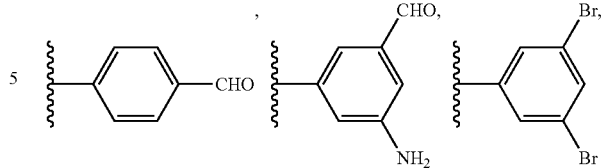
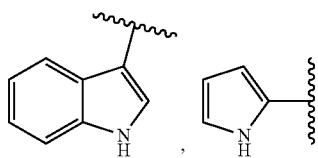
and, R₃ is selected from the group consisting of H, —OH, —NH₂.
2. The compound, or the pharmaceutically acceptable salt thereof, according to claim 1, wherein R₁ is selected from the group consisting of
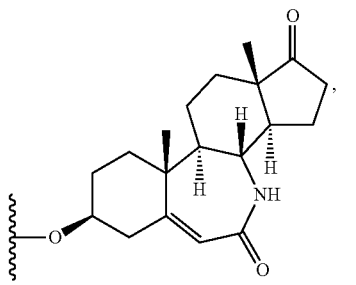
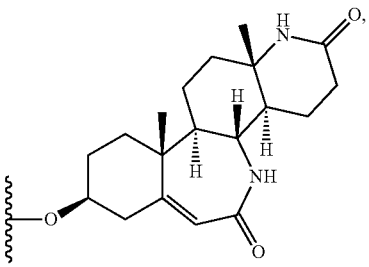
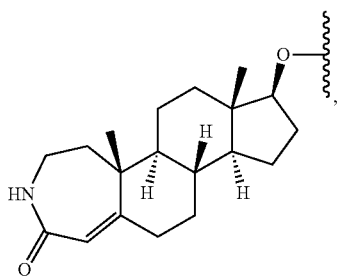
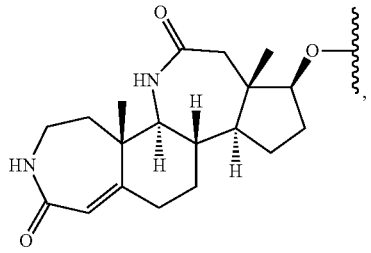

33
-continued
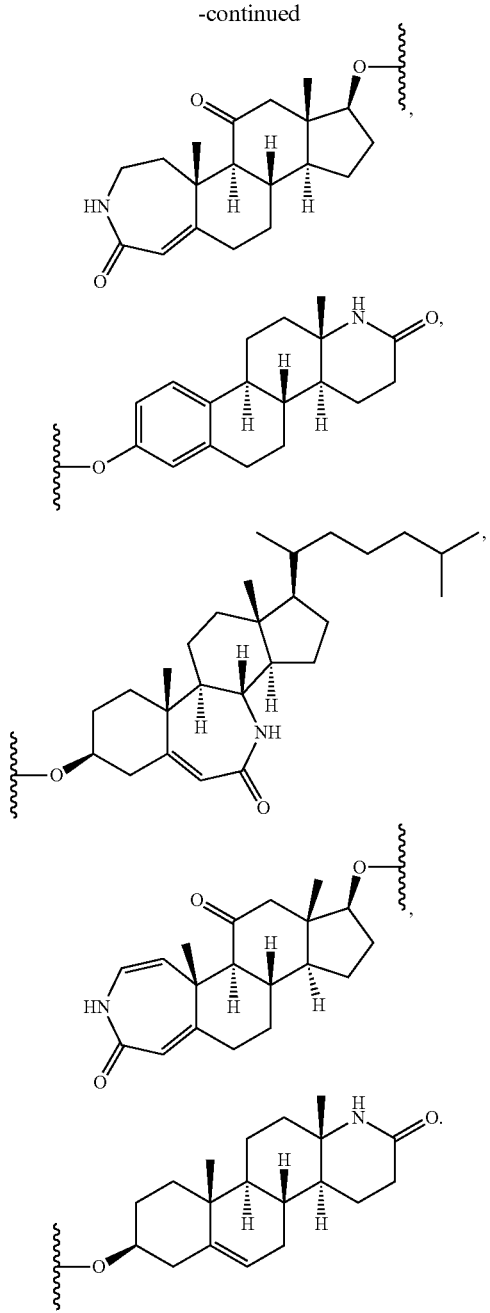
3. The compound, or the pharmaceutically acceptable salt thereof, according to claim 2, wherein $R_1$ is selected from the group consisting of
34
-continued
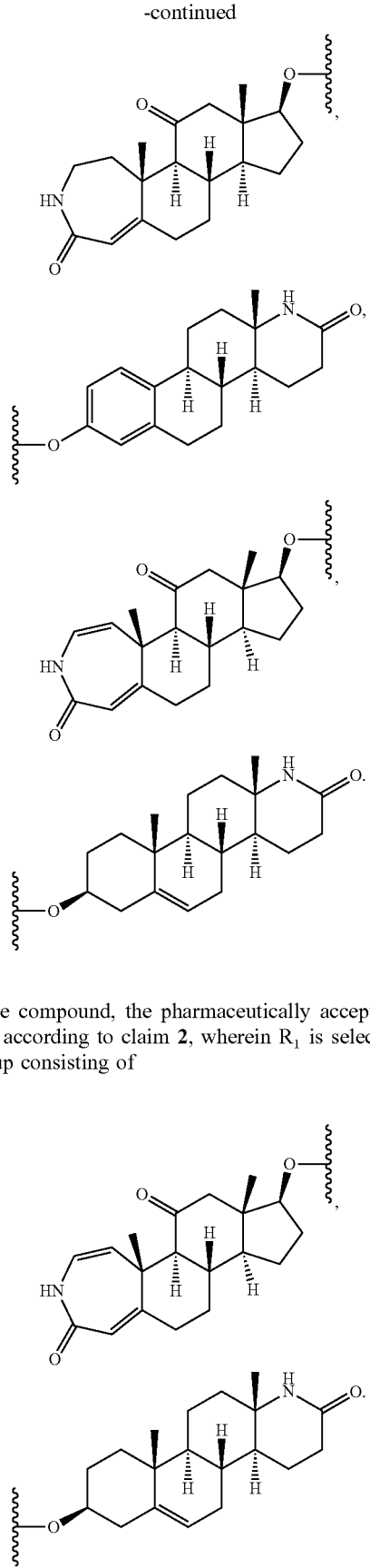
4. The compound, the pharmaceutically acceptable salt thereof, according to claim 2, wherein $R_1$ is selected from the group consisting of 5. The compound, or the pharmaceutically acceptable salt thereof, according to claim 1, wherein $R_2$ is selected from the group consisting of H, —CH$_3$, —CH=CH$_2$, —CH$_2$CH$_3$, —CH$_2$CH$_2$CH$_3$.

6. The compound, or the pharmaceutically acceptable salt thereof, according to claim 5, wherein $R_2$ is H.

7. The compound, or the pharmaceutically acceptable salt thereof, according to claim 1, wherein $R_3$ is H.

8. The compound, or the pharmaceutically acceptable salt thereof, according to claim 1, wherein $R_3$ is —NH$_2$.

9. A method of treating one of ovarian cancer, breast cancer, prostate cancer or leukemia, the method comprising:

administering to a patient a compound of formula (I), or a pharmaceutically acceptable salt thereof,

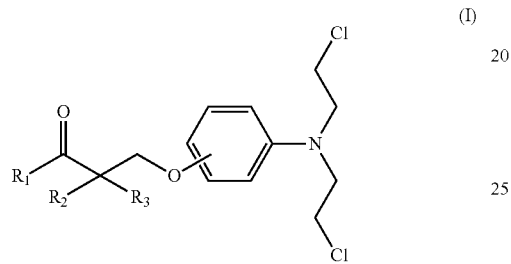

(I)

wherein $R_1$ is selected from the group consisting of

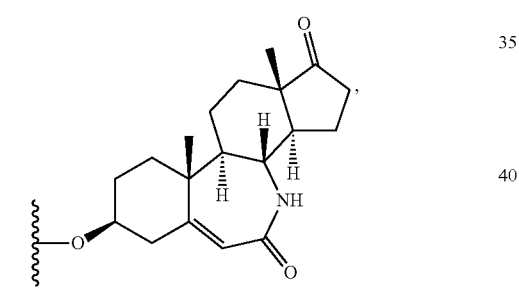

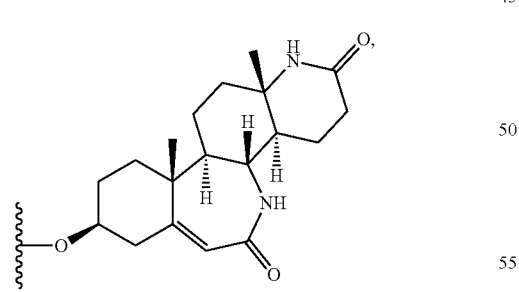

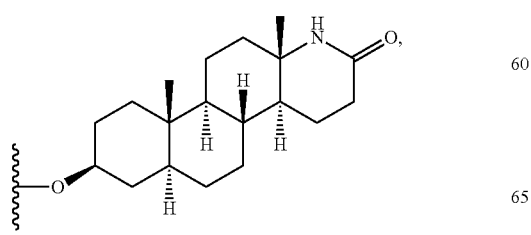

-continued

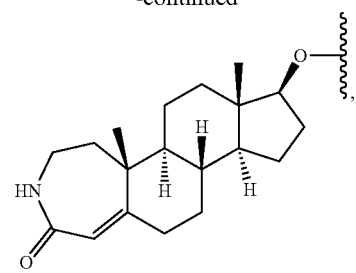

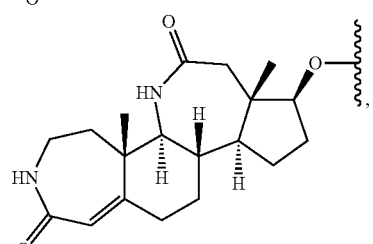

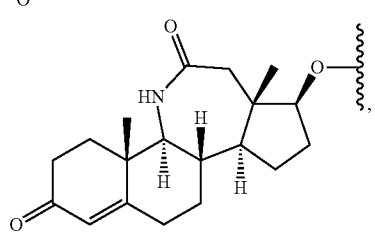

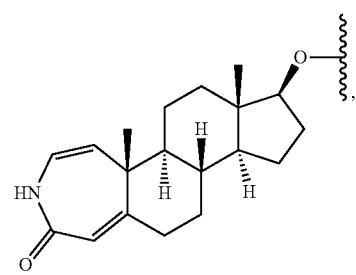

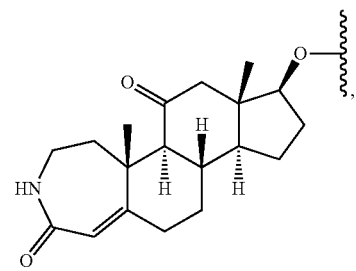

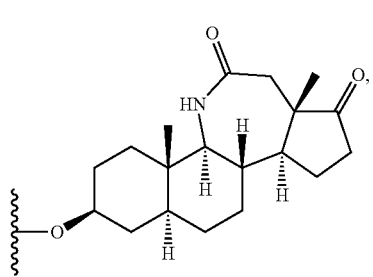

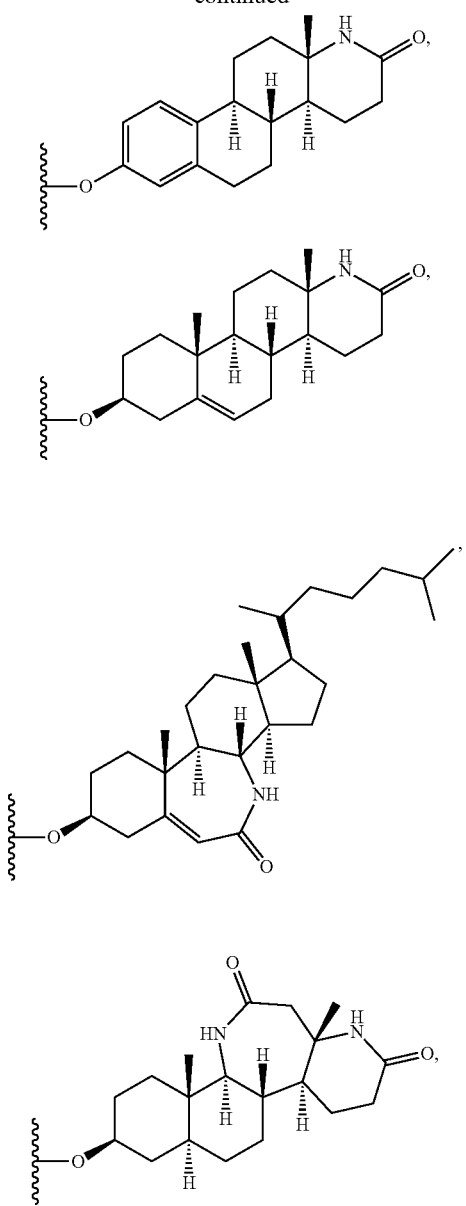
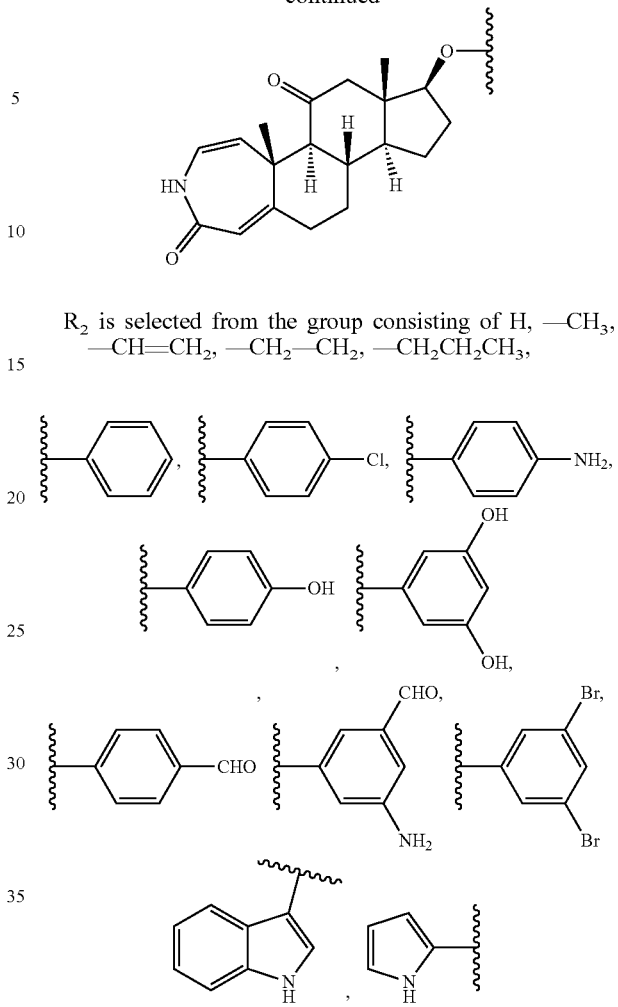
and,
$R_3$ is selected from the group consisting of H, —OH, —NH$_2$.
10. The pharmaceutical composition comprising a compound, or the pharmaceutically acceptable salt thereof, according to claim 1 and a pharmaceutically acceptable carrier.
* * * * *